US012698502B2

(12) United States Patent
Sood et al.

(10) Patent No.: US 12,698,502 B2
(45) Date of Patent: Aug. 4, 2026

(54) RNA APTAMERS AND USE THEREOF FOR TREATING CANCER

(71) Applicants: Board of Regents, The University of Texas System, Austin, TX (US); Consiglio Nazionale delle Ricerche, Rome (IT)

(72) Inventors: Anil K. Sood, Houston, TX (US); Paola Amero, Houston, TX (US); Gabriel Lopez-Berestein, Houston, TX (US); Vittorio De Franciscis, Rome (IT)

(73) Assignees: BOARD OF REGENTS, THE UNIVERSITY OF TEXAS SYSTEM, Austin, TX (US); CONSIGLIO NAZIONALE DELLE RICERCHE, Rome (IT)

( * ) Notice: Subject to any disclaimer, the term of this patent is extended or adjusted under 35 U.S.C. 154(b) by 810 days.

(21) Appl. No.: 17/995,343

(22) PCT Filed: Apr. 1, 2021

(86) PCT No.: PCT/US2021/025348

§ 371 (c)(1),
(2) Date: Oct. 3, 2022

(87) PCT Pub. No.: WO2021/202858

PCT Pub. Date: Oct. 7, 2021

(65) Prior Publication Data

US 2023/0167453 A1 Jun. 1, 2023

Related U.S. Application Data

(60) Provisional application No. 63/004,187, filed on Apr. 2, 2020.

(51) Int. Cl.
*C12N 15/115* (2010.01)
*A61P 35/00* (2006.01)

(52) U.S. Cl.
CPC ............ *C12N 15/115* (2013.01); *A61P 35/00* (2018.01); *C12N 2310/16* (2013.01); *C12N 2310/322* (2013.01)

(58) Field of Classification Search
None
See application file for complete search history.

(56) References Cited

U.S. PATENT DOCUMENTS 5,972,599 A * 10/1999 Tasset .................. C07K 14/495 536/25.4
7,964,356 B2 * 6/2011 Zichi .................... C12Q 1/6811 536/23.1
9,125,930 B2 9/2015 De Franciscis et al.
9,234,202 B2 1/2016 Cerchia et al.
2018/0134746 A1 * 5/2018 Giangrande ........... A61K 9/007

FOREIGN PATENT DOCUMENTS

WO WO 2018/218223 A1 11/2018
WO WO 2018/218231 A1 11/2018

OTHER PUBLICATIONS

LaFargue et al. Overcoming adaptive resistance to anti-VEGF therapy by targeting CD5L abstract, proceedings of the american association for cancer research annual meeting:Cancer Res 2019;79(13Supp):abstract 194, Mar. 29-Apr. 3, 2019 (Year: 2019).*
Aldag, J. et al., "2'-Fluoro-Pyrimidine-Modified RNA Aptamers Specific for Lypopolysaccharide Binding Protein (LBP)," *International Journal of Molecular Sciences*, 19 (2018): 1-15.
Aran, G. et al., "CD5L is upregulated in hepatocellular carcinoma and promotes liver cancer cell proliferation and antiapoptotic responses by binding to HSPA5 (GRP78)," *FASEB J.*, 32.7 (2018): 3878-3891.
Bergers. G. et al., "Modes of resistance to anti-angiogenic therapy," *Nat Rev Cancer*, 8 (2008): 592-603.
LaFargue, C. J. et al., "Overcoming adaptive resistance to anti-VEGF therapy by targeting CD5L," *Proceedings of the American Association for Cancer Research*, 60 (2019): 48-49, Abstract #194.
LaFargue, C. J. et al., "Overcoming adaptive resistance to anti-VEGF therapy by targeting CD5L," *The University of Texas MD Anderson Cancer Center*, 2019, poster.
Liu, M. et al., "Aptamer selection and applications for breast cancer diagnostics and therapy," *Journal of Nanobiotechnology*, 15 (2017): 1-16.
Kuwata, K. et al., "AIM Inhibits Apoptosis of T Cells and NKT Cells in Corynebacterium-Induced Granuloma Formation in Mice," *American Journal of Pathology*, 162 (2003): 837-847.
Maehara, N. et al., "Circulating AIM Prevents Hepatocellular Carcinoma through Complement Activation," *Cell Reports*, 9 (2014): 61-74.
PCT International Preliminary Report on Patentability issued in International Patent Application No. PCT/US2021/025348, mailed Oct. 13, 2022.
PCT International Search Report and Written Opinion issued in International Patent Application No. PCT/US2021/025348, mailed Aug. 13, 2021.
Qu, P. et al., "Myeloid-Specific Expression of Api6/AIM/Spα Induces Systemic Inflammation and Adenocarcinoma in the Lung," *The Journal of Immunology*, 182 (2009): 1648-1659.
Sanjurjo, L. et al., "AIM/CD5L: a key protein in the control of immune homeostasis and inflammatory disease," *Journal of Leukocyte Biology*, 98 (2015): 173-184.
Silverstein, R. L. et al., "CD36, a Scavenger Receptor Involved in Immunity, Metabolism, Angiogenesis, and Behavior," *Sci Signal*, 2 (2009): 1-14.
Zhou, G. et al., "Aptamer-Based Therapeutic Approaches to Target Cancer Stem Cells," *Theranostics*, 7.16 (2017): 3948-3961.

* cited by examiner

*Primary Examiner* — Brian Whiteman
(74) *Attorney, Agent, or Firm* — pH IP Law

(57) ABSTRACT

Provided herein are RNA aptamers targeting CD5L. Further provided herein are methods of use thereof for the treatment of a disease or disorder, such as cancer.

16 Claims, 41 Drawing Sheets

Specification includes a Sequence Listing.

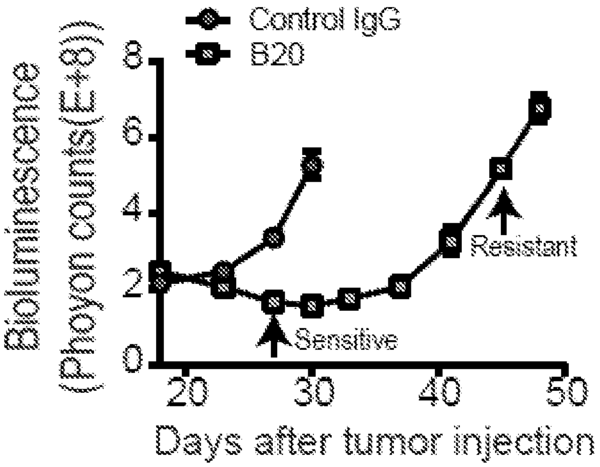
FIG. 1A
| Symbol | Fold change |
|---|---|
| LYZ2 | 7.08 |
| CCL6 | 7.1 |
| F10 | 9.02 |
| ARG1 | 14.85 |
| PRG4 | 12.66 |
| ALOX15 | 13.63 |
| CD5L | 28.48 |
| C230085N | -35.74 |
| GPR171 | -25.64 |
| CXCR5 | -22.72 |
| BTLA | -19.6 |
| IGH | -18.18 |
| IGH | -17.54 |
| ITGB2 | -16.12 |
FIG. 1B
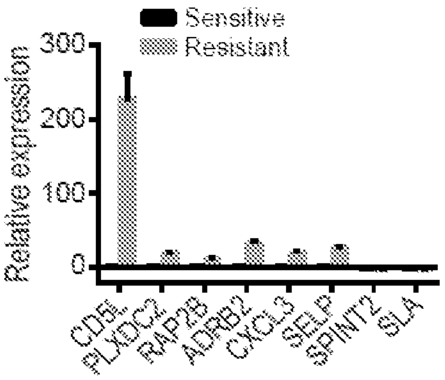
FIG. 1C CD5L expression (OS, HG)

P=0.013

Survival (%)

100
80
60
40
20
0

CD5L Low
CD5L High 0 82 164 246 328 410

Follow up (Months) # at risk

| | | | | | |
|---|---|---|---|---|---|
| 30 | 8 | 3 | 2 | 1 | score=2 |
| 24 | 2 | 1 | 0 | 0 | score=3 |

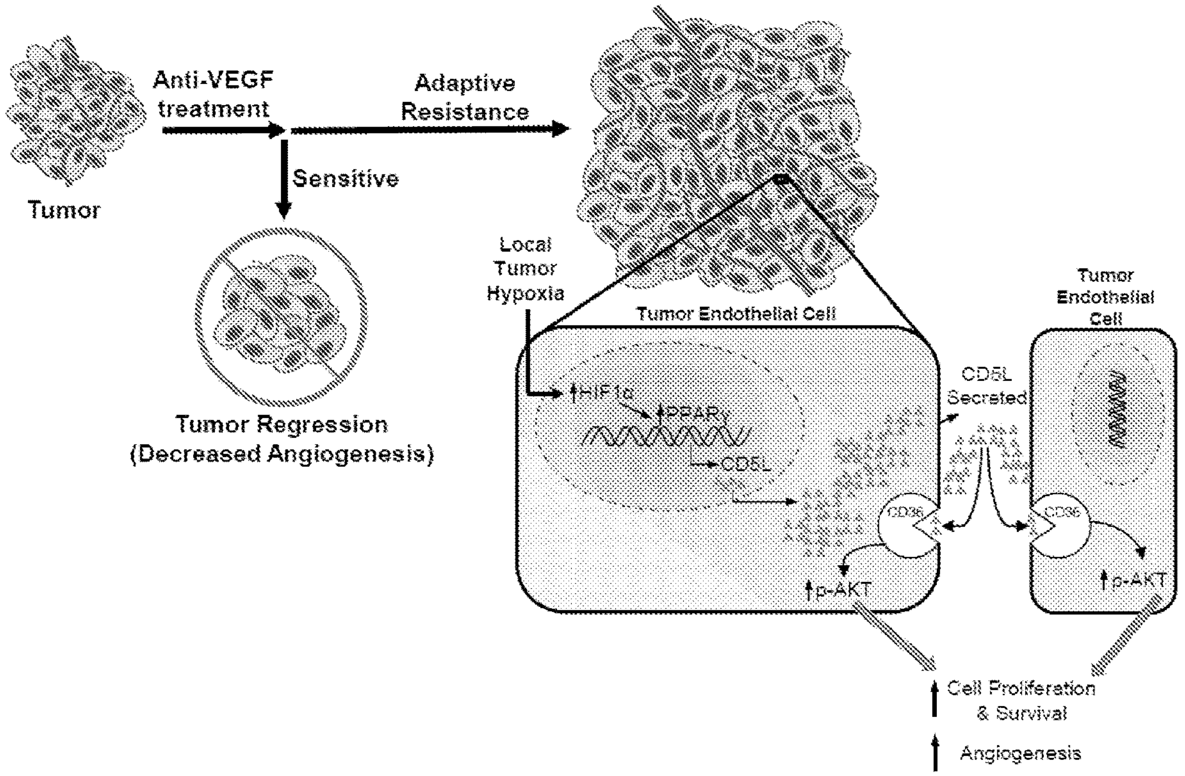

FIG. 7

CD5L promoter sequence

```
  1 ATAACAAATC TGTATATTGG ACCCTCTGCT TAGCAGTGAG AAAGCAGGTT TGAAGACAAT
 61 AAAGCCAGGC CTGTATGTGG AGATTGGCAC CATGACCCTG GATTATGTTT TATGGGATAT
121 GCCTCCAAGG GCAACTCTGC ATTTATCCCA TGGCCTCTGG CTTCCAAATT TTCTAGGCAC
181 TTCCCTCTGG GGTAAAGGAA TCAAAATTGG CTTATTTCCC TTGCAAACCA TCCTTGGCGA
241 CTAAGTACTG CCTTGTCTTC TACTGAGAGA TGGCCATATT TTTGGCACCT GCCTTTCCTT
301 GTGGGAGGTG TTTCCTCTGT TTACATAGCA AAGGGGCTGT AGGAGAGACA GACGGAGCTG
361 GACTTACAGC AGAACCAAGT CATGATAGCC TGTTTCTATT TTGTTTTCAG CATTTTTCCG
421 CCAGTTCTGG CCACCTCCTT TCCTCTGGAA CATGCTGATT TCAGCAAGTC CAGCTCTGTC
481 AGCTCTGCCC CCCGAGTCTA TTGGTTTCTG ATCATCTGAT AATGCTTTGC CTGCACTCAG
541 GACCTGTCTT TGTCCCTCCT CTTAACATAC TTGCAGCTAA AACTAAATAT TGCTGCTTGG
601 GGACCTCCTT CTAGCCTTAA ATTTCAGCTC ATCACCTTCA CCTGCCTTGG TCATGGCTCT
661 GCTATTCTCC TTGATCCTTG GTGAGTATCT CTGCACCTGT TGGTTTAGGC TTCAGAGTTT
721 TCTGGCACTT TGATTAGGAG AACTTTCTCC CCGC
```

FIG. 8

S5 full lenght sequence Free Energy: -23.3

Phylogenetic Tree Second Round of Selection

Full Lenght Sequence Allignament

```
        10        20        30        40        50        60        70        80
Ss5  AGACAAGAAGAAACGCUCAAG----CGAAGGCUU--GACCACAAACCA-CAGAAAGGCAAGGUCGCGCCGCGGUCGACAGGAGC
S11  AGACAAGAAGAAACGCUCAAA----AAGAGGGGGCAGAGCA-AGACC---CGAAAAGAGAGAGCGGACGCGAAUUCGACAGGAGC
S23  AGACAAGAAGAAACGCUCAAA----AAGAGA-GAAGGAGAA-GAACCAGCAAAAAGAGAGAGCAGAGCCAGAGUCGACAGGAGC
S29  AGACAAGAAGAAACGCUCAAUGAUCCGAGA GGCCGAACAGAGACUU CGUUA GACACCUU    GCAGCGGUCGACAGG  G
S76  AGACAAGAAGAAACGCUCAAUGAUCCGAGA-GGCCGAACAGAGACUU-CGUUA-GACAGGUU---GCAGCCUUCGACAGGAGC
Cluster
Consensus
```

FIG. 13B

Sequence Ss5 Free Energy: -23.3

Sequence S11 Free Energy: -14.8

Sequence S23 Free Energy: -13.5

Sequence S29 Free Energy: -13.8

From FIG. 14D

60

G A C G C G A A U U C G A 70 C A G G A G C U C G C A 80 C A A C A

From FIG. 14D

Sequence S76 Free Energy: -15.7

RNA APTAMERS AND USE THEREOF FOR TREATING CANCER

This application is a national phase application under 35 U.S.C. § 371 of International Application No. PCT/US2021/025348, filed Apr. 1, 2021, which claims benefit of priority to U.S. Provisional Application Ser. No. 63/004,187, filed Apr. 2, 2020, the entire contents of each of which are hereby incorporated by reference.

STATEMENT REGARDING FEDERALLY SPONSORED RESEARCH

This invention was made with government support under Grant No. CA217685 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Apr. 1, 2021, is named UTFCP1465WO_ST25.txt and is 2.03 kilobytes in size.

BACKGROUND

1. Field

The present invention relates generally to the fields of cancer biology and medicine. More particularly, it concerns RNA aptamers and use thereof.

2. Description of Related Art

Angiogenesis is known to play an important role in tumor development and growth (Folkman, 1971). This complex process relies on the careful orchestration of many factors including vascular endothelial growth factor (VEGF) and its receptor (VEGFR), fibroblast growth factor (FGF), and others (Weis and Cheresh, 2011). Many anti-angiogenesis drugs, particularly focused on the VEGF/VEGFR pathway, have been developed and approved for cancer treatment. While many patients benefit from such therapies, virtually all patients will eventually develop relapse or progression of disease. Understanding and overcoming adaptive changes to anti-VEGF drugs represents an opportunity to further enhance the efficacy of these drugs and potentially delay or prevent adaptive resistance (Bergers and Hanahan, 2008).

SUMMARY

In one embodiment, provided herein are RNA aptamers that selectively bind to CD5 antigen-like precursor (CD5L). In some aspects, the RNA aptamers have dissociation constants for CD5L of about 50 nM, 45 nM, 40 nM, 35 nM, 30 nM, 25 nM, 20 nM, 15 nM, or 10 nM or less.

In some aspects, the RNA aptamers further comprise at least one modified nucleotide. In some aspects, the aptamers comprise at least one 2'-modified nucleotide. In some aspects, at least one nucleotide in an RNA aptamer is chemically modified with 2'-fluoropyrimidine. In some aspects, 2, 3, 4, or 5 pyrimidines in an RNA aptamer are chemically modified with 2'-fluoropyrimidine. In some aspects, all of the pyrimidines in an RNA aptamer are chemically modified with 2'-fluoro pyrimidine.

In some aspects, the aptamers are covalently linked to a carrier selected from the group consisting of a soluble polymer, a biodegradable polymer, polyethylene glycol, and cholesterol. In some aspects, the aptamers are 40-100 nucleotides in length.

In some aspects, the aptamers comprise a nucleotide sequence at least 90%, at least 91%, at least 92%, at least 93%, at least 94%, at least 95%, at least 96%, at least 97%, at least 98% or at least 99% identical to a nucleotide sequence selected from the group consisting of SEQ ID NOs: 1-5 and a truncate thereof. In some aspects, the aptamers comprise a nucleotide sequence selected from the group consisting of SEQ ID NOs: 1-5 and a truncate thereof.

In some aspects, the aptamers comprise a nucleotide sequence at least 90%, at least 91%, at least 92%, at least 93%, at least 94%, at least 95%, at least 96%, at least 97%, at least 98% or at least 99% identical to the nucleotide sequence of SEQ ID NO: 6. In some aspects, the aptamers comprise a nucleotide sequence of SEQ ID NO: 6.

In some aspects, the aptamers are single-stranded. In some aspects, the aptamers fold into at least one hairpin-like structure. In some aspects, the aptamers further comprise a detectable label.

In one embodiment, provided are compositions comprising a therapeutically effective amount of an RNA aptamer of any one of the present embodiments, and a pharmaceutically acceptable diluent or vehicle. In some aspects, the compositions are provided for use as a medicament for treating a cancer in a patient.

In one embodiment, provided are methods of treating a cancer in a patient comprising administering an effective amount of an RNA aptamer of any one of the present embodiments to the patient. In some aspects, the RNA aptamer is administered intravenously. In some aspects, the cancer is breast cancer, colon cancer, prostate cancer, lung cancer, gastric cancer, ovarian cancer, endometrial cancer, renal cancer, hepatocellular cancer, thyroid cancer, uterine cancer, esophageal carcinoma, squamous cell carcinoma, leukemia, osteosarcoma, melanoma, glioblastoma or neuroblastoma. In some aspects, the cancer is ovarian cancer.

In some aspects, the patient is further administered a second anticancer therapy. The second anticancer therapy may be an anti-angiogenic therapy, such as, for example, an anti-VEGF therapy. In some aspects, the RNA aptamer results in increased efficacy of the anti-angiogenic therapy. In some aspects, the second anticancer therapy comprises chemotherapy, immunotherapy, surgery, radiotherapy, or biotherapy.

In some aspects, the patient's cancer has been determined to overexpress CD5L. In some aspects, the patient's serum has been determined to have an elevated level of CD5L. In some aspects, the patient's cancer has recurred following anti-angiogenic therapy. In some aspects, the patient's cancer has been determined to be resistant to anti-VEGF therapy.

In one embodiment, provided herein are methods for the detection of CD5L comprising (a) incubating a sample with an RNA aptamer of any of the present embodiments; and (b) measuring the binding of the RNA aptamer to the sample. In some aspects, the sample is blood, serum, saliva, biopsy, urine, or cerebrospinal fluid.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "essentially" is to be understood that methods or compositions include only the specified steps or materials and those that do not materially affect the basic and novel characteristics of those methods and compositions.

The term "substantially free of" is used to 98% of the listed components and less than 2% of the components to which composition or particle is substantially free of The terms "substantially" or "approximately" as used herein may be applied to modify any quantitative comparison, value, measurement, or other representation that could permissibly vary without resulting in a change in the basic function to which it is related.

The term "about" means, in general, within a standard deviation of the stated value as determined using a standard analytical technique for measuring the stated value. The terms can also be used by referring to plus or minus 10% of the stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1M. Upregulation of CD5L in anti-VEGF Therapy Resistant Endothelial Cells Promotes Angiogenesis and Migration. (FIG. 1A) Schematic representing time points at which tumors isolated during course of B20 treatment. Tumor progression identified by increase in bioluminescence. (FIG. 1B) Heat map from gene expression profile demonstrating fold change in B20 resistant compared to sensitive tumors. (FIG. 1C) Fold change of RNA expression of select genes in both B20 sensitive and resistant tumors. (FIG. 1D) CD5L staining in endothelial cells from mouse tumors sensitive (L) and resistant (R) to B20. (FIG. 1E) CD5L protein expression in RF24 endothelial cells containing CD5L overexpressing plasmid versus empty vector (EV). (FIG. 1F) Cell proliferation in RF24 endothelial cells containing CD5L overexpressing plasmid versus EV. (FIGS. 1G&1H) Tube formation (FIG. 1G) and cell migration (FIG. 1H) in RF24 endothelial cells containing CD5L overexpressing plasmid versus EV. (FIG. 1I) Concentration of CD5L in media collected from RF24 endothelial cells containing CD5L overexpressing plasmid. (FIGS. 1J-1M) CD5L protein expression (FIG. 1J), cell proliferation (FIG. 1K), tube formation (FIG. 1L), and cell migration (FIG. 1M) in RF24 endothelial cells treated with siCD5L versus siControl. (*P<0.05, P<0.01, *P<0.001). Bars represent mean±sd. EV-empty vector.

(FIGS. 2A&2B) CD5L mRNA (FIG. 2A) and protein expression (FIG. 2B) in RF24 endothelial cells containing PPAR-γ overexpressing plasmid versus (EV). (FIG. 2N) Chromatin immunoprecipitation (ChIP) analysis of the CD5L promoter using an anti-PPAR-γ antibody under hypoxic and normoxic conditions. (*P<0.05, P<0.01, *P<0.001). Bars represent mean±sd.

(FIG. 3A) Reverse phase protein array (RPPA) analysis of RF24 endothelial cells treated with CD5L protein versus control. (FIG. 3B) AKT pathway activation measured by phospho-AKT/AKT in RF24 cells after exogenous CD5L protein treatment. (FIGS. 3C-3E) AKT pathway activation (FIG. 3C), tube formation (FIG. 3D), and cell migration (FIG. 3E) in RF24 cells treated with CD5L protein and either LY294002 (PI3K inhibitor) or DMSO. (FIG. 3F) CD36 mRNA expression in RF24 cells treated with CD5L protein. (FIG. 3G) AKT pathway activation in RF24 cells treated with siCD36. (FIG. 3H) PPAR-γ mRNA expression in RF24 cells treated with CD5L protein. (FIGS. 3I&3J) Cell viability of RF24 cells at increasing concentrations of bevacizumab with the additional of either CD5L protein (FIG. 3I) or siCD5L (FIG. 3J). (ns—not significant, *P<0.05, P<0.01, *P<0.001). Bars represent mean±sd.

(FIG. 4A) Photographs of representative mice from each group in wild-type (WT) and TIE2CrePPARγflox/flox (KO) mice. (FIGS. 4B&4C) Tumor weight (g) and number of tumor nodules (mean±sd., as denoted by error bars). Significant difference in tumor weight is denoted by the asterisk (*P<0.05, P<0.01, *P<0.001). (FIGS. 4D&4E) Statistical analysis of paraffin slides for the expression of Ki67 and CD31. Five fields per slide and at least three slides (5 slides for each group, WT and KO) were examined. Bars represent mean±sd. P<0.01 and *P<0.001. (FIG. 4F) Survival plot for B20, anti-VEGF treatment. B20 was injected intraperitoneal twice weekly at a dose of 5 mg/kg. (FIG. 4G) Expression of p-AKT relative to AKT in tumor samples from WT versus TIE2CrePPARγflox/flox (KO) mice (p-AKT to AKT ratio determined after normalization of AKT to vinculin).

(FIG. 5A) Expression of p-AKT, Gai1 in RF24 resistant cells after treatment with S76.T aptamer. (FIGS. 5B&5C) S76.T significantly reduces number of nodes (FIG. 5B) and cell migration (FIG. 5C) compared with scrambled aptamer in RF24 resistant cells (mean±sd.; P<0.01; *P<0.001). (FIG. 5D) Proliferation assay in RF24 endothelial cells. RF24 endothelial cells were treated with S76.T alone or in combination with Bevacizumab (mean±sd.; *P<0.001). (FIG. 5E) Schematic of xenograft adaptive resistant tumor model. S76.T aptamer was injected intravenously every 3 days starting on day 38, after 21 days of B20 treatment. (FIG. 5F) Photographs of representative mouse from each group in scramble and S76.T mice. (FIGS. 5G&5H) Tumor weight (g) and number of tumor nodules (mean±sd., as denoted by error bars). Significant difference in tumor weight is denoted by the asterisk (P<0.01, *P<0.001) (FIGS. 5I&5J) Statistical analysis of paraffin slides for the expression of Ki67 and CD31. Five fields per slide and at least three slides (5 slides for each group, WT and KO) were examined. Bars represent mean±sd. * P<0.001.

(FIGS. 6A&6B) CD5L protein expression measured by immunohistochemistry (IHC) (FIG. 6A) and serum protein levels (FIG. 6B) in ovarian cancer patients classified as either responsive or non-responsive to bevacizumab (mean±sd, as denoted by error bars). (FIG. 6C) Representative images of low (upper) and high (lower) CD5L protein expression in tumor endothelial cells from human ovarian cancer patients. (FIG. 6D) Kaplan Meier curve of overall survival in high-grade serous ovarian cancer patients stratified according to CD5L protein expression level, as measured by IHC (see FIG. 6C).

FIG. 7. Mechanism of CD5L Induced AVA Resistance. Anti-VEGF treatment may initially cause tumor regression via decreased angiogenesis (lower tumor—single blood vessel); however, adaptive resistance frequently emerges after time leading to tumor growth and increased angiogenesis (larger tumor with many blood vessels). Inset demonstrates tumor endothelial cell showing that local tumor hypoxia leads to an increase in CD5L secretion via overexpression of the transcription factor PPAR-γ. Secreted CD5L binds to the CD36 receptor causing an activation of the AKT pathway leading ultimately to increased cell proliferation and angiogenesis.

FIG. 8. Promoter Sequence of CD5L. PPAR-γ binding site identified in red. Lower image represents CD5L promoter construct with critical base pairs in PPAR-γ binding highlighted (CTCT).

FIGS. 13A-13B. Phylogenetic Tree of the Second Round of Selection and Alignment of S5, S11, S23, S29 and S76 Sequences. (FIG. 13A) Phylogenetic tree of second round of Tandem Protein-SELEX. (FIG. 13B) Alignment of S5, S11, S23, S29 and S76 sequences.

(FIGS. 15A&15B) Binding affinity of full-length S76 sequence by MTS (FIG. 15A) and prediction of secondary structure (FIG. 15B; SEQ ID NO: 5) by using RNA structure version 5.1. (FIGS. 15C&15D) Binding affinity of truncated S76 (S76.T) sequence by MTS (FIG. 15C) and prediction of secondary structure (FIG. 15D; SEQ ID NO: 6) by using RNA structure version 5.1.

DETAILED DESCRIPTION

Figure 1D:
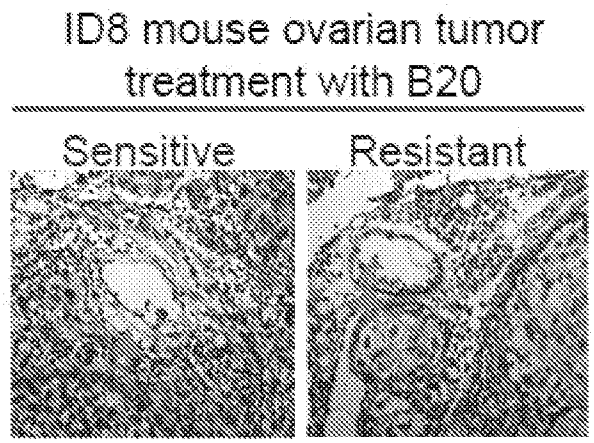

Anti-angiogenic treatment targeting the vascular endothelial growth factor (VEGF) pathway is a powerful tool to combat tumor growth and progression; however, drug-resistance frequently occurs. CD5 antigen-like precursor (CD5L) is identified herein as an important protein in the response to anti-angiogenic treatment leading to the emergence of adaptive resistance. Using a newly developed RNA-aptamer targeting CD5L, the pro-angiogenic effects of CD5L overexpression was abated in both in vitro and in vivo settings. Additionally, CD5L overexpression in cancer patients was shown to be associated with bevacizumab resistance and worse overall survival. These findings implicate CD5L as a major driver of adaptive resistance to anti-angiogenic therapy, and modalities to target CD5L have important clinical utility.

Anti-angiogenic therapies are an integral component in the treatment of cancer. While drugs such as bevacizumab, an anti-VEGF monoclonal antibody, are approved by the FDA for cancer therapy, a major limitation of anti-VEGF drugs is the high frequency of adaptive resistance, rendering treatment ineffective. This is particularly important as the indications for use of this drug expand. Herein, it was shown that increased endothelial CD5L expression is an important driver of resistance to anti-VEGF therapy and that modalities used to negate its effect (e.g., an RNA aptamer) can be employed to reverse the resistant phenotype. Incorporation of anti-CD5L agents into clinical trials may reveal a feasible approach for lengthening the efficacy of anti-VEGF therapies.

To examine potential mechanisms underlying resistance to anti-VEGF antibody (AVA) therapy, mouse models were used to identify tumors that demonstrated growth subsequent to a period of initial response. Specifically, orthotopic mouse models of ovarian cancer designed to develop adaptive resistance after treatment with the anti-VEGF antibody B20, which targets both mouse and human VEGF-A, were established. The genomic profiles of tumor-associated endothelial cells collected at pre-treatment, maximal response, and at tumor progression were examined, and substantially elevated CD5L levels were found at the time of progression. CD5L (or AIM—apoptosis inhibitor expressed by macrophages) was previously identified as a soluble protein secreted primarily from macrophages in lymphoid tissues during an inflammatory response (Sanjurjo et al., 2015). While additional roles of CD5L have been discovered since, those related specifically to endothelial cells and angiogenesis remain unknown. Here, data are presented implicating CD5L expression in adaptive resistance to bevacizumab. It was also demonstrated that neutralizing CD5L using an aptamer targeting CD5L blocked adaptive resistance to anti-angiogenic therapy, indicating anti-CD5L is a potential new therapeutic strategy for overcoming resistance to bevacizumab and other anti-angiogenesis therapies.

I. TARGETING OF CD5L

The data provided herein identify CD5L as an important mediator of AVA resistance, a previously unrecognized role which functions in promoting tumor angiogenesis. From a conceptual perspective, hypoxia incurred due to prolonged VEGF blockade ultimately drives the overexpression of CD5L through the upregulation of the transcription factor PPAR-γ. Through analysis of the downstream pathways, prominent activation of the PI3K/AKT pathway with increased CD5L signaling in tumor endothelial cells was demonstrated (FIG. 7). Importantly, blocking CD5L through multiple modalities could restore response to anti-VEGF therapy.

Anti-VEGF drugs are currently approved for the treatment of many different cancer types. Unfortunately, although the initial response rates are high with these therapies, most patients develop resistant disease within weeks-to-months. The mechanisms underlying such adaptive resistance are likely to be multi-factorial and are not fully understood. One such mechanism involves the upregulation of pro-angiogenic factors other than VEGF in response to AVA treatment, such as fibroblast growth factor 1 and ephrin A1 (Casanovas et al., 2005). Additionally, tumors treated with AVA compounds adapt by increasing their invasive potential without relying on novel vessel generation (Norden et al., 2008, Narayana et al 2009). Regardless of the exact mechanism, the phenomenon that tumor endothelial cells adapt to their specific microenvironment is now well accepted. Therefore, a systematic approach was taken, whereby mRNA profiling from tumor endothelial cells from responder vs. non-responder mice was carried out and CD5L was identified as the mostly highly expressed mRNA in treatment-resistant endothelial cells.

Initially named for its anti-apoptotic role on leukocytes (Miyazaki et al., 1999), CD5L has since been implicated as a key regulator of inflammatory responses, particularly through its effect on macrophages. It has also been shown to be involved in a variety of cellular processes including atherosclerosis, infection, and cancer (Sanjurjo et al., 2015). Although CD5L is secreted primarily by macrophages, it has been shown to have diverse roles in the immune system. Mice deficient in CD5L have reduced lymphocytes in liver granulomas when challenged with heat-killed *C. parvum* compared to wild type mice (Kuwata et al., 2003). Additionally, in vitro studies using liver T- and natural killer T (NKT)-cells from mice exposed to *C. parvum* showed significant inhibition of apoptosis after treatment with recombinant CD5L (Kuwata et al., 2003). CD5L has also been shown to induce formation of bronchoalveolar adenocarcinoma in a transgenic mouse model with CD5L overexpressing myeloid cells (Qu et al., 2009). Interestingly, CD5L seems to have a protective role in mouse hepatocellular carcinoma through its interaction with CD55, CD59, and Crry, leading to subsequent complement activation and induced necrotic death of hepatocytes (Maehara et al., 2014). The scavenger receptor CD36 has been implicated as the primary cell-surface receptor for CD5L (Kurokawa et al., 2010) and although CD36 is expressed on endothelial cells, whether CD5L played an important role in endothelial survival was not known (Silverstein and Febbraio, 2009). Silencing CD36 prevented the pro-angiogenic phenotype associated with increased CD5L expression, iterating the necessity of both CD5L and intact CD36 to develop AVA resistance.

Through analysis of an ovarian cancer cohort, a clinical correlation between CD5L overexpression and bevacizumab resistance was demonstrated. This suggests that upregulation of CD5L by tumor endothelial cells is an integral component of the adaptive resistance mechanism against bevacizumab treatment. Concordantly, patients who had higher levels of CD5L also had worse overall survival, likely due to the decreased anti-tumor effect of bevacizumab seen in the resistant setting.

Adaptive resistance to anti-VEGF therapy is a complex mechanism programmed by tumors to allow for continued survival. As increasing data emerges regarding the molecular pathways responsible for this phenomenon, it will be important to carefully select the critical components for development of novel therapeutics and subsequent clinical trials. CD5L is herein identified as an integral protein in the adaptive response to anti-VEGF treatment and strategies aimed at targeting it could benefit patients being treated with anti-angiogenic drugs.

II. RNA APTAMERS

Disclosed herein are RNA aptamer molecules that modulate, and preferably, that inhibit the activities of CD5L. Optionally, the aptamers are identified through a method known in the art as Systematic Evolution of Ligands by EXponential Enrichment, SELEX. The RNA aptamers of the present invention preferably comprise 2'-fluoro-pyrimidines to enhance resistance to nuclease degradation. The affinities of the present RNA aptamers for CD5L preferably range from $K_d$S of about 100 pM to about 100 nM.

The term "RNA analog" is meant to refer to a polymeric molecule, which in addition to containing ribonucleosides as its units, also contains at least one of the following: 2'-deoxy, 2'-halo (including 2'-fluoro), 2'-amino (preferably not substituted or mono- or disubstituted), 2'-mono-, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available "chain terminator" or "non-extendible" analogs (at the 3'-end of the RNA), or labels such as $^{32}P$, $^{33}P$ and the like. All of the foregoing can be incorporated into an RNA using the standard synthesis techniques disclosed herein.

The terms "binding activity" and "binding affinity" are meant to refer to the tendency of a ligand molecule to bind or not to bind to a target. The energetics of said interactions are significant in "binding activity" and "binding affinity" because they define the necessary concentrations of interacting partners, the rates at which these partners are capable of associating, and the relative concentrations of bound and free molecules in a solution. The energetics are characterized herein through, among other ways, the determination of a dissociation constant, $K_d$. An aptamer of the present invention having a preferred $K_d$ value is further evaluated in an assay for effects on the target. For example, a $K_i$ value as described herein below can be determined for the aptamer and the target.

The term "ligand" as used herein refers to a molecule or other chemical entity having a capacity for binding to a target. A ligand can come from any source, including libraries, particularly combinatorial libraries, such as aptamer libraries, phage display libraries, or any other library as would be apparent to one of ordinary skill in the art after review of the disclosure of the present invention presented herein.

As used herein, a "target" or "target molecule" refers to a biomolecule that could be the focus of a therapeutic drug strategy or diagnostic assay, including, without limitation, proteins or portions thereof, enzymes, peptides, enzyme inhibitors, hormones, carbohydrates, glycoproteins, lipids, phospholipids, nucleic acids, and generally, any biomolecule capable of turning a biochemical pathway on or off or modulating it, or which is involved in a predictable biological response. Any target that is of sufficient size to be specifically recognized by an oligonucleotide sequence can be used as the target. Thus, glycoproteins, proteins, carbohydrates, membrane structures, receptors, organelles, and the like can be used as the complexation targets.

As used herein, "specifically binding oligonucleotides", "nucleic acid ligands" or "aptamers" refer to oligonucleotides having specific binding regions that are capable of forming complexes with an intended target molecule in an environment where other substances in the same environment are not complexed to the oligonucleotide. The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ for the aptamer with respect to the target will be 2-fold, preferably 5-fold, more preferably 10-fold less than $K_d$ with respect to target and the unrelated material or accompanying material in the environment. Even more preferably the $K_d$ will be 50-fold less, more preferably 100-fold less, and more preferably 200-fold less.

In general, aptamers preferably comprise about 10 to about 100 nucleotides, preferably about 15 to about 40 nucleotides, more preferably about 20 to about 40 nucleotides, in that oligonucleotides of a length that falls within these ranges are readily prepared by conventional techniques. Optionally, aptamers can further comprise a minimum of approximately 6 nucleotides, preferably 10, and more preferably 14 or 15 nucleotides, that are necessary to effect specific binding. The only apparent limitations on the binding specificity of the target/oligonucleotide couples of the invention concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

As used herein, "aptamer" refers in general to either an oligonucleotide of a single defined sequence or a mixture of said oligonucleotides, wherein the mixture retains the properties of binding specifically to the target molecule. Thus, as used herein "aptamer" denotes both singular and plural sequences of oligonucleotides, as defined hereinabove. The term "aptamer" is meant to refer to a single- or double-stranded nucleic acid which is capable of binding to a protein or other molecule, and thereby disturbing the protein's or other molecule's function.

Structurally, the aptamers of the invention are specifically binding oligonucleotides, wherein "oligonucleotide" is as defined herein. As set forth herein, oligonucleotides include not only those with conventional bases, sugar residues and internucleotide linkages, but also those that contain modifications of any or all of these three moieties.

"Single-stranded" oligonucleotides, as the term is used herein, refers to those oligonucleotides that contain a single covalently linked series of nucleotide residues.

"Oligonucleotide" or "oligomer" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base or abasic nucleotides.

An "RNA aptamer" is an aptamer comprising ribonucleoside units. "RNA aptamer" is also meant to encompass RNA analogs as defined herein above.

When a number of individual, distinct aptamer sequences for a single target molecule have been obtained and sequenced, the sequences can be examined for "consensus sequences". As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences with nucleotide sequences or polymers of hundreds of bases long interspersed between the consensus sequences. Consensus sequences can be identified by sequence comparisons between individual aptamer species, which comparisons can be aided by computer programs and other tools for modeling secondary and tertiary structure from sequence information. Generally, the consensus sequence will contain at least about 3 to 20 nucleotides, more commonly from 6 to 10 nucleotides.

As used herein "consensus sequence" means that certain positions, not necessarily contiguous, of an oligonucleotide are specified. By specified it is meant that the composition of the position is other than completely random. Not all oligonucleotides in a mixture can have the same nucleotide at such position; for example, the consensus sequence can contain a known ratio of particular nucleotides. For example, a consensus sequence might consist of a series of four positions wherein the first position in all members of the mixture is A, the second position is 25% A, 35% T and 40% C, the third position is T in all oligonucleotides, and the fourth position is G in 50% of the oligonucleotides and C in 50% of the oligonucleotides.

The term "truncate" refers to an aptamer that has been truncated by deletion of nucleotides but still possesses a desired or even improved binding characteristic. Truncates can vary in length in accordance with the length of the starting aptamer and as defined above for the term "aptamer". Truncations in the truncate can occur in fixed or variable regions, or both fixed and variable regions, of the starting aptamer.

In a representative embodiment of the present invention, an RNA aptamer is synthesized on a solid support column, using conventional techniques. The final DMT-group is removed from the resulting RNA aptamer. Alternately, if large-scale synthesis is used, the RNA aptamer can be made by scale-up of the solid support method or the RNA aptamer can be made by using solution phase techniques, particularly if the desired end-product is a relatively short oligonucleotide. A starting material for the synthesis process can be a 5'-non-tritylated RNA oligoribo-nucleotide or analog of the desired primary structure, which preferably can have protected bases, and which is preferably bound to a solid-support. Any conventionally used protecting groups can be used. Typically $N_6$-benzoyl is used for adenine, $N_4$-benzoyl for cytosine, $N_2$-isobutyryl for guanine and $N_2$-benzoyl for 2-amino purine. Other useful protecting groups include phenoxyacetyl (PAC) and t-butoxyacetyl (TAC). Conveniently, the more base labile protection groups should be used for the synthesis of the RNA or analog fragment; those of ordinary skill in the art know these groups. Such groups can help to prevent hydrolysis of the generated tri- or diphosphates, which are generally quite stable under basic conditions, but could be subject to some hydrolysis. Other envisioned modifications include but are not limited to the incorporation of bioavailability enhancing molecules such as PEG or cholesterol via a covalent linkage.

III. PHARMACEUTICAL COMPOSITIONS

Also provided herein are pharmaceutical compositions and formulations comprising an RNA aptamer and a pharmaceutically acceptable carrier.

The pharmaceutical composition may comprise the present RNA aptamer in a pharmaceutically effective amount in the pharmaceutical composition. The medicament further comprises preferably suitable carrier material, excipients and the like. If necessary, the medicinal product may contain one or more other active ingredients. The active compounds can be also coupled to the RNA aptamer, i.e., covalently or non-covalently bound. Suitable formulations and dosage forms are known in the art or can be prepared in a routine manner according to the prior art. The aptamers of the invention can for example be bound to nanoparticles which are loaded with other active ingredients, whereby a targeted delivery of the active ingredients is made possible.

Pharmaceutical compositions and formulations as described herein can be prepared by mixing the active ingredients (such as a lipid or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn— protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.).

IV. METHODS OF TREATMENT

The present invention provides methods of treating a cancer patient with a CD5L-targeting RNA aptamer as provided herein. Such treatment may also be in combination with another therapeutic regime, such as chemotherapy or immunotherapy. In some cases, the patient's cancer may overexpress CD5L. In some cases, the level of CD5L in the patient's serum may be elevated. In some cases, the patient's cancer may be bevacizumab resistant. In some cases, the patient's cancer may have recurred following bevacizumab treatment.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The methods described herein are useful in treating cancer. Generally, the terms "cancer" and "cancerous" refer to or describe the physiological condition in mammals that is typically characterized by unregulated cell growth. More specifically, cancers that are treated in connection with the methods provided herein include, but are not limited to, solid tumors, metastatic cancers, or non-metastatic cancers. In certain embodiments, the cancer may originate in the lung, kidney, bladder, blood, bone, bone marrow, brain, breast, colon, esophagus, duodenum, small intestine, large intestine, colon, rectum, anus, gum, head, liver, nasopharynx, neck, ovary, pancreas, prostate, skin, stomach, testis, tongue, or uterus.

The cancer may specifically be of the following histological type, though it is not limited to these: neoplasm, malignant; carcinoma; non-small cell lung cancer; renal cancer; renal cell carcinoma; clear cell renal cell carcinoma; lymphoma; blastoma; sarcoma; carcinoma, undifferentiated;

meningioma; brain cancer; oropharyngeal cancer; nasopharyngeal cancer; biliary cancer; pheochromocytoma; pancreatic islet cell cancer; Li-Fraumeni tumor; thyroid cancer; parathyroid cancer; pituitary tumor; adrenal gland tumor; osteogenic sarcoma tumor; neuroendocrine tumor; breast cancer; lung cancer; head and neck cancer; prostate cancer; esophageal cancer; tracheal cancer; liver cancer; bladder cancer; stomach cancer; pancreatic cancer; ovarian cancer; uterine cancer; cervical cancer; testicular cancer; colon cancer; rectal cancer; skin cancer; giant and spindle cell carcinoma; small cell carcinoma; small cell lung cancer; papillary carcinoma; oral cancer; oropharyngeal cancer; nasopharyngeal cancer; respiratory cancer; urogenital cancer; squamous cell carcinoma; lymphoepithelial carcinoma; basal cell carcinoma; pilomatrix carcinoma; transitional cell carcinoma; papillary transitional cell carcinoma; adenocarcinoma; gastrointestinal cancer; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma with squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; an endocrine or neuroendocrine cancer or hematopoietic cancer; pinealoma, malignant; chordoma; central or peripheral nervous system tissue cancer; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular; mycosis fungoides; mantle cell lymphoma; Waldenstrom's macroglobulinemia; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and hairy cell leukemia.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

Likewise, an effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, previous therapy, the patient's clinical history and response to the agent, and the discretion of the physician. The agent may be suitably administered to the patient at one time or over a series of treatments.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

An aptamer may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an RNA aptamer is "A" and another anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin, nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins;

mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

B. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, Infection Immun., 66(11):5329-5336, 1998; Christodoulides et al., Microbiology, 144(Pt 11):3027-3037, 1998); cytokine therapy, e.g., interferons α, β, and γ, IL-1, GM-CSF, and TNF (Bukowski et al., Clinical Cancer Res., 4(10):2337-2347, 1998; Davidson et al., J. Immunother., 21(5):389-398, 1998; Hellstrand et al., Acta Oncologica, 37(4):347-353, 1998); gene therapy, e.g., TNF, IL-1, IL-2, and p53 (Qin et al., Proc. Natl. Acad. Sci. USA, 95(24):14411-14416, 1998; Austin-Ward and Villaseca, Revista Medica de Chile, 126(7):838-845, 1998; U.S. Pat. Nos. 5,830,880 and 5,846,945); and monoclonal antibodies, e.g., anti-CD20, anti-ganglioside GM2, and anti-p185 (Hanibuchi et al., Int. J. Cancer, 78(4):480-485, 1998; U.S. Pat. No. 5,824,311). It is contemplated that one or more anti-cancer therapies may be employed with the antibody therapies described herein.

In some embodiment, the immune therapy could be adoptive immunotherapy, which involves the transfer of autologous antigen-specific T cells generated ex vivo. The T cells used for adoptive immunotherapy can be generated either by expansion of antigen-specific T cells or redirection of T cells through genetic engineering. Isolation and transfer of tumor specific T cells has been shown to be successful in treating melanoma. Novel specificities in T cells have been successfully generated through the genetic transfer of transgenic T cell receptors or chimeric antigen receptors (CARs). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. CARs have successfully allowed T cells to be redirected against antigens expressed at the surface of tumor cells from various malignancies including lymphomas and solid tumors.

In one embodiment, the present application provides for a combination therapy for the treatment of cancer wherein the combination therapy comprises adoptive T cell therapy and/or a checkpoint inhibitor. In one aspect, the adoptive T cell therapy comprises autologous and/or allogenic T-cells. In another aspect, the autologous and/or allogenic T-cells are targeted against tumor antigens. Checkpoint inhibitors are discussed in greater detail above.

Immunomodulatory agents include immune checkpoint inhibitors, agonists of co-stimulatory molecules, and antagonists of immune inhibitory molecules. The immunomodulatory agents may be drugs, such as small molecules, recombinant forms of ligand or receptors, or antibodies, such as human antibodies (e.g., International Patent Publication WO2015/016718; Pardoll, *Nat Rev Cancer,* 12(4): 252-264, 2012; both incorporated herein by reference). Known inhibitors of immune checkpoint proteins or analogs thereof may be used, in particular chimerized, humanized, or human forms of antibodies may be used. As the skilled person will know, alternative and/or equivalent names may be in use for certain antibodies mentioned in the present disclosure. Such alternative and/or equivalent names are interchangeable in the context of the present disclosure. For example, it is known that lambrolizumab is also known under the alternative and equivalent names MK-3475 and pembrolizumab.

Co-stimulatory molecules are ligands that interact with receptors on the surface of the immune cells, e.g., CD28, 4-1BB, OX40 (also known as CD134), ICOS, and GITR. As an example, the complete protein sequence of human OX40 has Genbank accession number NP 003318. In some embodiments, the immunomodulatory agent is an anti-OX40 antibody (e.g., a human antibody, a humanized antibody, or a chimeric antibody), an antigen binding fragment thereof, an immunoadhesin, a fusion protein, or oligopeptide. Anti-human-OX40 antibodies (or VH and/or VL domains derived therefrom) suitable for use in the present methods can be generated using methods well known in the art. Alternatively, art recognized anti-OX40 antibodies can be used. An exemplary anti-OX40 antibody is PF-04518600 (see, e.g., WO 2017/130076). ATOR-1015 is a bispecific antibody targeting CTLA4 and OX40 (see, e.g., WO 2017/182672, WO 2018/091740, WO 2018/202649, WO 2018/002339).

Another co-stimulatory molecule that can be targeted in the methods provided herein is ICOS, also known as CD278. The complete protein sequence of human ICOS has Genbank accession number NP_036224. In some embodiments, the immune checkpoint inhibitor is an anti-ICOS antibody (e.g., a human antibody, a humanized antibody, or a chimeric antibody), an antigen binding fragment thereof, an immunoadhesin, a fusion protein, or oligopeptide. Anti-human-ICOS antibodies (or VH and/or VL domains derived therefrom) suitable for use in the present methods can be generated using methods well known in the art. Alternatively, art recognized anti-ICOS antibodies can be used. Exemplary anti-ICOS antibodies include JTX-2011 (see, e.g., WO 2016/154177, WO 2018/187191) and GSK3359609 (see, e.g., WO 2016/059602).

Yet another co-stimulatory molecule that can be targeted in the methods provided herein is glucocorticoid-induced tumour necrosis factor receptor-related protein (GITR), also known as TNFRSF18 and AITR. The complete protein sequence of human GITR has Genbank accession number NP_004186. In some embodiments, the immunomodulatory agent is an anti-GITR antibody (e.g., a human antibody, a humanized antibody, or a chimeric antibody), an antigen binding fragment thereof, an immunoadhesin, a fusion protein, or oligopeptide. Anti-human-GITR antibodies (or VH and/or VL domains derived therefrom) suitable for use in the present methods can be generated using methods well known in the art. Alternatively, art recognized anti-GITR antibodies can be used. An exemplary anti-GITR antibody is TRX518 (see, e.g., WO 2006/105021).

Immune checkpoint proteins that may be targeted by immune checkpoint blockade include adenosine A2A receptor (A2AR), B7-H3 (also known as CD276), B and T lymphocyte attenuator (BTLA), CCL5, CD27, CD38, CD8A, CMKLR1, cytotoxic T-lymphocyte-associated protein 4 (CTLA-4, also known as CD152), CXCL9, CXCR5, HLA-DRB1, HLA-DQA1, HLA-E, killer-cell immunoglobulin (KIR), lymphocyte activation gene-3 (LAG-3, also known as CD223), Mer tyrosine kinase (MerTK), NKG7, programmed death 1 (PD-1), programmed death-ligand 1 (PD-L1, also known as CD274), PDCD1LG2, PSMB10, STAT1, T cell immunoreceptor with Ig and ITIM domains (TIGIT), T-cell immunoglobulin domain and mucin domain 3 (TIM-3), and V-domain Ig suppressor of T cell activation (VISTA, also known as C10orf54). In particular, immune checkpoint inhibitors targeting the PD-1 axis and/or CTLA-4 have received FDA approval broadly across diverse cancer types.

In some embodiments, a PD-1 binding antagonist is a molecule that inhibits the binding of PD-1 to its ligand binding partners. In a specific aspect, the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, a PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or an oligopeptide. Exemplary antibodies are described in U.S. Pat. Nos. 8,735,553, 8,354,509, and 8,008,449, all of which are incorporated herein by reference. Other PD-1 axis antagonists for use in the methods provided herein are known in the art, such as described in U.S. Patent Application Publication Nos. 2014/0294898, 2014/022021, and 2011/0008369, all of which are incorporated herein by reference.

In some embodiments, a PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Another immune checkpoint protein that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA-4 is similar to the T-cell co-stimulatory protein, CD28, and both molecules bind to CD80 and CD86, also called B7-1 and B7-2 respectively, on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide. Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in U.S. Pat. No. 8,119,129; PCT Publn. Nos. WO 01/14424, WO 98/42752, WO 00/37504 (CP675,206, also known as tremelimumab; formerly ticilimumab); U.S. Pat. No. 6,207,156; Hurwitz et al. (1998) *Proc Natl Acad Sci USA,* 95(17): 10067-10071; Camacho et al. (2004) *J Clin Oncology,* 22(145): Abstract No. 2505 (antibody CP-675206); and Mokyr et al. (1998) *Cancer Res,* 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2, and CDR3 domains of the VL region of ipilimumab. In another embodiment, the antibody competes for binding with and/or binds to the same epitope on CTLA-4 as the above-mentioned antibodies. In another embodiment, the antibody has an at least about 90% variable region amino acid sequence identity with the above-mentioned antibodies (e.g., at least about 90%, 95%, or 99% variable region identity with ipilimumab). Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

Another immune checkpoint protein that can be targeted in the methods provided herein is lymphocyte-activation gene 3 (LAG-3), also known as CD223. The complete protein sequence of human LAG-3 has the Genbank accession number NP-002277. LAG-3 is found on the surface of activated T cells, natural killer cells, B cells, and plasmacytoid dendritic cells. LAG-3 acts as an "off" switch when bound to MHC class II on the surface of antigen-presenting cells. Inhibition of LAG-3 both activates effector T cells and inhibitor regulatory T cells. In some embodiments, the immune checkpoint inhibitor is an anti-LAG-3 antibody (e.g., a human antibody, a humanized antibody, or a chimeric antibody), an antigen binding fragment thereof, an immunoadhesin, a fusion protein, or oligopeptide. Anti-human-LAG-3 antibodies (or VH and/or VL domains derived therefrom) suitable for use in the present methods can be generated using methods well known in the art. Alternatively, art recognized anti-LAG-3 antibodies can be used. An exemplary anti-LAG-3 antibody is relatlimab (also known as BMS-986016) or antigen binding fragments and variants thereof (see, e.g., WO 2015/116539). Other exemplary anti-LAG-3 antibodies include TSR-033 (see, e.g., WO 2018/201096), MK-4280, and REGN3767. MGD013 is an anti-LAG-3/PD-1 bispecific antibody described in WO 2017/019846. FS118 is an anti-LAG-3/PD-L1 bispecific antibody described in WO 2017/220569.

Another immune checkpoint protein that can be targeted in the methods provided herein is V-domain Ig suppressor of T cell activation (VISTA), also known as C10orf54. The complete protein sequence of human VISTA has the Genbank accession number NP_071436. VISTA is found on white blood cells and inhibits T cell effector function. In some embodiments, the immune checkpoint inhibitor is an anti-VISTA3 antibody (e.g., a human antibody, a humanized antibody, or a chimeric antibody), an antigen binding fragment thereof, an immunoadhesin, a fusion protein, or oligopeptide. Anti-human-VISTA antibodies (or VH and/or VL domains derived therefrom) suitable for use in the present methods can be generated using methods well known in the art. Alternatively, art recognized anti-VISTA antibodies can be used. An exemplary anti-VISTA antibody is JNJ-61610588 (also known as onvatilimab) (see, e.g., WO 2015/097536, WO 2016/207717, WO 2017/137830, WO 2017/175058). VISTA can also be inhibited with the small molecule CA-170, which selectively targets both PD-L1 and VISTA (see, e.g., WO 2015/033299, WO 2015/033301).

Another immune checkpoint protein that can be targeted in the methods provided herein is CD38. The complete protein sequence of human CD38 has Genbank accession number NP_001766. In some embodiments, the immune checkpoint inhibitor is an anti-CD38 antibody (e.g., a human antibody, a humanized antibody, or a chimeric antibody), an antigen binding fragment thereof, an immunoadhesin, a fusion protein, or oligopeptide. Anti-human-CD38 antibodies (or VH and/or VL domains derived therefrom) suitable for use in the present methods can be generated using methods well known in the art. Alternatively, art recognized anti-CD38 antibodies can be used. An exemplary anti-CD38 antibody is daratumumab (see, e.g., U.S. Pat. No. 7,829,673).

Another immune checkpoint protein that can be targeted in the methods provided herein is T cell immunoreceptor with Ig and ITIM domains (TIGIT). The complete protein sequence of human TIGIT has Genbank accession number NP_776160. In some embodiments, the immune checkpoint inhibitor is an anti-TIGIT antibody (e.g., a human antibody, a humanized antibody, or a chimeric antibody), an antigen binding fragment thereof, an immunoadhesin, a fusion protein, or oligopeptide. Anti-human-TIGIT antibodies (or VH and/or VL domains derived therefrom) suitable for use in the present methods can be generated using methods well known in the art. Alternatively, art recognized anti-TIGIT antibodies can be used. An exemplary anti-TIGIT antibody is MK-7684 (see, e.g., WO 2017/030823, WO 2016/028656).

Other immune inhibitory molecules that can be targeted for immunomodulation include STAT3 and indoleamine 2,3-dioxygenase (IDO). By way of example, the complete protein sequence of human IDO has Genbank accession number NP_002155. In some embodiments, the immunomodulatory agent is a small molecule IDO inhibitor. Exemplary small molecules include BMS-986205, epacadostat (INCB24360), and navoximod (GDC-0919).

C. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

V. KITS

Kits are envisioned containing RNA aptamers of the present invention. The kit may comprise reagents required for the delivery of the RNA aptamer. The kit may also comprise a suitable container means, which is a container that will not react with components of the kit, such as an eppendorf tube, a syringe, a bottle, or a tube. The container may be made from sterilizable materials such as plastic or glass. The kit may further include an instruction sheet that outlines the procedural steps of the methods, such as the same procedures as described herein or are otherwise known to those of ordinary skill.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

TABLE 1

| Materials | | |
|---|---|---|
| REAGENT or RESOURCE | SOURCE | IDENTIFIER |
| Experimental Models: Cell Lines | | |
| SKOV3ip1 | MDA Cell Line Core | N/A |
| ID8 | Dr. Roby at UKansas | N/A |
| RF24 | ABM (Applied Biological Materials) | Catalog Number T0003 |
| HEK293T | ATCC | CRL-3216 |
| Experimental Models: Organisms/Strains | | |
| Mouse: Ppar$\gamma^{fl/fl}$; Tie$^{2-}$Cre$^{+/-}$ female and male | Dr Yihong Wan, University of Texas Southwestern, (10 mice/group) | N/A |
| uMouse: Female athymic nude mice (NCr-nu) | Taconic (10 mice/group) | N/A |
| Chemicals, Peptides, and Recombinant Proteins | | |
| OCT | Miles, Inc., Elkhart, IN | Catalog Number 25608-930 |
| CD31 | Pharmingen, San Diego, CA | Catalog Number 557355 |
| Ki67 | Zymed, San Francisco, CA | Catalog number sc-23900 |
| RNeasy mini kit | Qiagen | Catalog Number 74104 |
| SYBR Green ER qPCR SuperMix Universal | Invitrogen, Carlsbad, CA | 4368708 |
| SiRNAs | Sigma-Aldrich | N/A |
| Lipofectamine 2000 | Lipofectamine | Catalog Number 11668027 |
| Human recombinant CD5L protein | Sino Biological, Beijing, China | Catalog Number 10791-H08H |
| Bevacizumab | Genetech | N/A |
| MTT reagent | Sigma-Aldrich | M2128 |
| Aptamer | Sigma-Aldrich | N/A |

TABLE 1-continued

| Materials | | |
|---|---|---|
| REAGENT or RESOURCE | SOURCE | IDENTIFIER |
| His-tagged VEGF-A | Abnova, Taiwan | Catalog Number P5816 |
| His-tagged CD19 | Life Technologies, Carlsbad, CA | Catalog Number 11880H08H250 |
| 6-His Peptide tagged | BioLegend, San Diego, CA | Catalog Number 931601 |
| DNA library | TriLink Biotechnologies, San Diego, CA | Fitzwater T. and Polisky B. (1996) |
| M-MuLV Reverse Transcriptase | Roche, Indianapolis, IN | Catalog Number 11062603001 |
| $Ni^{2+}$ NTA Magnetic Agarose Beads | Qiagen, Hilden, Germany | Catalog Number 36111 |
| TRIzol Reagent | Life Technologies, Carlsbad, CA | Catalog Number 15596026 |
| TOPO Cloning | Life Technologies, Carlsbad, CA | Catalog Number K4500-01SC, K4550-01SC, K4600-01SC |
| Antibodies: Expressed in HEK293 suspension cells and purified using protein A affinity resin to purity >95%. | | |
| AKT | Cell Signaling Technologies | Catalog Number 4691/9272 |
| Phospho-AKT | Cell Signaling Technologies | Catalog Number 4060 |
| PPARγ | Cell Signaling Technologies | Catalog Number 2430 |
| Anti-human CD5L | Santacruz Biotechnology | Catalog Number sc-514281 |
| | R&D Systems | Catalog Number AF2797 |
| β-actin | Sigma-Aldrich | A5441 |
| Vinculin | Sigma-Aldrich | V9131 |
| Anti-Rabbit secondary antibodies conjugated with horseradish peroxidase. | Sigma-Aldrich | NA934 |
| Anti-Mouse secondary antibodies conjugated with horseradish peroxidase. | Sigma-Aldrich | NA931 |
| pLenti-C-mGFP-human CD5L vector | Origene | RC206528L2 |
| Critical Commercial Assays | | |
| Click-iT EdU Assay Kit | Invitrogen | Catalogue number C10632 |
| CD5L ELISA Kit | Mybiosource, San Diego, CA, USA | Catalogue Number MBS2024653 |
| Verso cDNA kit | Thermo Scientific | Catalogue number AB1453B |
| RNeasy mini kit | Qiagen | Catalogue number 74106 |
| EZ ChIPTM kit | Millipore, Temecula, CA | Catalogue number 17-371 |
| Software and Algorithms | | |
| GraphPad Prism 7.0. | SPSS version 12 for Windows statistical software | SPSS version 12 for Windows statistical software |
| Windows statistical software | SPSS version 12 for Windows statistical software | SPSS, Inc., Chicago, IL |
| Kaplan-Meier survival curves | SPSS version 12 for Windows statistical software | SPSS version 12 for Windows statistical software |
| ClustalW2 software | N/A | N/A |
| TreeVieX program | N/A | N/A |
| Monolith NT.115 | NanoTemper Technologies GmbH, Munchen, Germany | Stoltenburg R et al. PLoS One. 2015 |

Cell Lines and Culture. Human epithelial ovarian cancer cell line SKOV3ip1 and mouse ovarian cancer cell line ID8 were grown as previously described (Pradeep et al., 2015). Human immortalized umbilical endothelial cells (RF24) were grown in MEM medium containing supplements (non-essential amino acids, sodium pyruvate, MEM vitamins, and glutamine; Life Technologies, Grand Island, NY). Cell culture was performed at 37° C. in a 5% $CO_2$ incubator with 95% humidity. For in vivo injections, cells were first washed with PBS twice, followed by trypsinization and centrifugation at 1,200 rpm for 5 min at 4° C. Cells were then reconstituted in serum-free Hank's balanced salt solution (Life Technologies). Only single-cell suspensions with >95% viability were used for in vivo experiments (as determined by trypan blue exclusion).

Quantitative Real-Time Reverse-Transcriptase PCR Validation. Quantitative real-time reverse-transcriptase PCR was carried out using 50 ng of total RNA isolated from cells using the RNeasy mini kit (Qiagen). Complementary DNA (cDNA) was synthesized from 0.5-1.0 μg of total RNA by using a Verso cDNA kit (Thermo Scientific). Quantitative PCR (qPCR) analysis was performed in triplicate by using the reported primers (Table 2) and the SYBR Green ER qPCR SuperMix Universal (Invitrogen, Carlsbad, CA) with the Bio-Rad Thermocycler (Bio-Rad Laboratories, Hercules, CA). Quantification was performed using the $2^{-\Delta\Delta CT}$ method normalizing to control for percent fold changes (Donninger et al., 2004).

using anti-human CD5L, p-AKT, AKT, and PPAR-γ antibodies, followed by appropriate secondary antibodies conjugated with horseradish peroxidase. Experiments were done in duplicate and repeated at least twice.

Cell Proliferation Assay. Cell proliferation experiments were performed using the Click-iT EdU Assay Kit (Invitrogen). Cells were seeded into 6-well plates and cultured in a phenol-red free Opti-MEM for 48 hours. Cells were then harvested for the assessment of proliferation after CD5L protein or siRNA CD5L treatment.

Enzyme-Linked Immunosorbent Assay. CD5L expression levels were determined using a CD5L ELISA Kit (Mybiosource, San Diego, CA, USA) following the manufacturer's recommendations for both cell culture media as well as human blood samples.

Lentivirus-Mediated CD5L Overexpression. The pLenti-C-mGFP-human CD5L vector (RC206528L2) was purchased form Origene (Rockville, MD). HEK293T cells were co-transfected with the pLenti-C-mGFP-human CD5L vector and packaging plasmids. After 48 hours, supernatant containing infectious viral particles was collected, filtered using 0.45 μm filters, and stored in aliquots at −80° C. To generate cells that ectopically overexpressed CD5L, RF24 cells were incubated for 48 hours with viral particles. Cells were then washed with PBS and further incubated in culture medium. After 48 hours, GFP positive cells were collected using the FACS Aria II sorter.

TABLE 2

]Quantita[tive-PCR primer lists

| No. | Primers | Sequence (5'-3') | |
|---|---|---|---|
| 1 | Human CD5L F | 5'-CTGCTTGTTCTCCTGAGCCC -3' | (SEQ ID NO: 8) |
| 2 | Human CD5L R | 5'-TCAAAGGGTCAGGGTTGAGC -3' | (SEQ ID NO: 9) |
| 3 | Human PPAR-γ F | 5'-GCCCTTTGGTGACTTTATGGA -3' | (SEQ ID NO: 10) |
| 4 | Human PPAR-γ R | 5'-GCAGCAGGTTGTCTTGGATG -3' | (SEQ ID NO: 11) |
| 5 | Human CD36 F | 5'-GAGAACTGTTATGGGGCTAT -3' | (SEQ ID NO: 12) |
| 6 | Human CD36 R | 5'-TTCAACTGGAGAGGCAAAGG -3' | (SEQ ID NO: 13) |
| 7 | Tie2 Cre transgene F | 5'-CGCATAACCAGTGAAACAGCATTGC-3' | (SEQ ID NO: 14) |
| 8 | Tie2 Cre transgene R | 5'-CCCTGTGCTCAGACAGAAATGAGA-3' | (SEQ ID NO: 15) |

siRNA Constructs and Delivery. siRNAs were ordered from Sigma-Aldrich (Woodlands, TX). Our siRNA control consisted of a non-silencing siRNA that did not share sequence homology with any known human mRNA based on a BLAST search. In vitro transient transfection was performed as previously described (Landen et al., 2005). In brief, siRNA (4 μg) was incubated with 10 μL of Lipofectamine 2000 transfection reagent (Lipofectamine) for 20 minutes at room temperature followed by the addition to cells cultured in 10 cm plates at 80% confluence.

Reverse Phase Protein Array (RPPA) and Western Blot Analysis. RF24 cells were cultured in the presence or absence of human recombinant CD5L protein (Sino Biological, Beijing, China). Corresponding cell lysate was then submitted for RPPA analysis. Western blot analysis was performed as previously reported (Pradeep et al., 2015, Haemmerle et al., 2017). Cell lysate of RF24 cells was collected after treatment with human recombinant CD5L protein and activation of AKT signaling was performed Induction of Bevacizumab-Resistance in RF24 Cells. Bevacizumab-resistant cell line were derived from original parental RF24 cell line by continuous exposure to bevacizumab. RF24 cells were treated with bevacizumab (1 mg/ml, IC50) for 72 h. This media was then removed and the cells were allowed to recover for 7 days. Cells were continuously maintained in the presence of bevacizumab at IC50 concentrations.

Drug Sensitivity Assay (MTT). Cells ($5\times10^3$) were seeded in 96-well plates and allowed to adhere overnight at 37° C. Briefly, following treatment of cells with Bevacizumab for 72 h, MTT reagent [3-(4,5-Dimethylthiazol-2-yl)-2,5-diphenyltetrazoliumbromide] was added to each well and incubated for 4 h at 37° C. Dimethylsulphoxide (DMSO) was added to each well and mixed for 5 min on an orbital shaker. Absorbance was recorded at 450 nm and sensitivity to bevacizumab was calculated based on cell proliferation measurements at 72 h.

Cell Migration Assay. Migration of RF24 cells was examined in the presence or absence of hCD5L siRNA or CD5L aptamer using Transwell 0.4 μm pore polycarbonate membrane inserts coated with 0.1% gelatin. After post-transfection of 48 hours with hCD5L siRNAs or after treatment with CD5L aptamer (40 μg/ml), RF24 cells ($1.0\times10^5$) in MEM serum-free medium were seeded into the upper chamber of the Transwell 0.4 μm pore polycarbonate membrane insert (Corning, Lowell, MA). CD5L protein (400 ng/ml) was also added to the cell suspension prior to seeding, where indicated above. The insert was then placed in a 24-well plate containing MEM medium with 15% serum in the lower chamber as chemoattractant. After allowing cells to migrate for 6 hours in a humidified chamber, those that had migrated were stained with hematoxylin and counted by light microscopy in five random fields (×200 original magnification) per sample. Experiments were done in duplicate and repeated three times.

Tube Formation Assay. Matrigel (12.5 mg/mL) was thawed at 4° C., and either 50 μL was quickly added to each well of a 96-well plate or 10 μL, to each well of a 15-well plate and then allowed to solidify for 30 min at 37° C. The wells were then incubated for 6 h at 37° C. with RF24 cells (5,000-6000 per well), which had previously been treated with either CD5L siRNA (for 48 h), PI3kinase inhibitor or AKT inhibitor (for 6 h), or CD5L aptamer (added at time of cell seeding). Where indicated above, CD5L protein (400 ng/ml) was also added at time of cell seeding. Experiments were performed in triplicate and repeated at least twice. Using an Olympus IX81 inverted microscope, five images per well were taken at ×100 magnification. The number of nodes (defined as at least three cells that formed a single point) and tubes (defined as a non-segmented circle formed from endothelial cells) per image was quantified. The highest and lowest values were removed from each group to account for cell clumping.

Promoter Analysis and Chromatin Immunoprecipitation (ChIP) Assay. RF24 cells were cultured in hypoxia condition for 16 h. After hypoxic culture, ChIP assays were performed by using EZ ChIP™ kit (Millipore, Temecula, CA) as described by the manufacturer. In brief, cross-linked cells were collected, lysed, sonicated, and subsequently subjected to immunoprecipitation with PPAR-γ (Cell signaling) antibody or IgG control. Immunocomplexes were collected with protein G agarose beads and eluted. Cross-links were reversed by incubating at 65° C. DNA was then extracted and purified for subsequent PCR amplification using gene-specific primers (Table 1).

Orthotopic in vivo Model of Ovarian Cancer. Female athymic nude mice (NCr-nu) were purchased from the NCI-Frederick Cancer Research and Development Center (Frederick, MD) and maintained as described previously (Landen et al., 2005). All mouse studies were approved by the Institutional Animal Care and Use Committee. Mice were cared for in accordance with guidelines set forth by the American Association for Accreditation of Laboratory Animal Care and the US Public Health Service Policy on Humane Care and Use of Laboratory Animals. For tumor cells injection, SKOV3ip1 cells ($1\times10^6$) were injected intraperitoneally. For CD5L aptamer therapy experiments, aptamer (administered intravenously) and B20 (administered intraperitoneally) were given once weekly at a dose of 5 mg/kg body weight. After mice were euthanized with $CO_2$, their tumor weight and number and distribution of tumor nodules was recorded. Individuals who performed the necropsies were blinded to the treatment group assignments. Tissue specimens were either fixed using 10% buffered formalin, OCT (Miles, Inc., Elkhart, IN) or snap-frozen in liquid nitrogen.

Immunohistochemical and Immunofluorescence Staining of Xenografts. Immunohistochemical analyses for cell proliferation (Ki67, 1:200, Zymed, San Francisco, CA) and MVD (CD31, 1:500, Pharmingen, San Diego, CA) were performed as described previously (Thaker et al., 2006, Lu et al., 2010). For statistical analyses, sections from 5 randomly selected tumors per group were stained, and 5 random fields per tumor were scored. Pictures were taken at ×200 or ×100 magnification. To quantify MVD in the mouse tumor samples, the number of blood vessels staining positive for CD31 was recorded in 10 random 0.159-$mm^2$ fields at ×200 magnification. To quantify Ki67 expression, the number of positive cells was counted in 10 random 0.159-$mm^2$ fields at ×100 magnification (Thaker et al., 2006, Lu et al., 2010). All staining was quantified by two investigators in a blinded fashion. Analysis of CD5L expression in tumor endothelial cells from our ovarian cancer cohort was scored as either 1 (negative), 2 (low), or 3 (high).

Tie2-cre; PPAR-γ Knockout Mice. $Pparg^{fl/fl}$; Tie2-$Cre^{+/-}$ female and male mice were generously provided by Dr Yihong Wan, (University of Texas Southwestern). To selectively delete PPAR-γ in endothelial cells, female were crossed with male to obtain the PPAR-γ conditional knockout mice. Genomic DNA was isolated from tail biopsies of the mouse. Tie2-cre transgene and floxed PPAR-γ allele were distinguished by PCR using primers (Table 1). For tumor cells injection, ID8 cells ($1\times10^6$) were injected intraperitoneally in Tie2-cre; PPAR-γ KO mice. After mice were euthanized with $CO_2$, their tumor weight and number and distribution of tumor nodules was recorded. Individuals who performed the necropsies were blinded to the treatment group assignments. Tissue specimens were either fixed using either 10% buffered formalin, OCT (Miles, Inc., Elkhart, IN) or snap-frozen in liquid nitrogen. For B20 therapy experiments, B20 was give twice weekly at a dose of 5 mg/kg body weight after 7 days from ID8 tumor injection. Depending on the experimental design, B20 treatment continued until either the planned endpoint was reached, or until mice became moribund or deceased.

Aptamer. S76.T and the scramble, used as a negative control, were modified with 2'-Fluoro Pyrimidines (2'-F Py) and purchased by Sigma Aldrich (St. Louis, MO).

```
S76.T:
                                        (SEQ ID NO: 6)
5' AGGUUGCAGCGUUCGACAGGAGGCUCACAACAG 3'

Scramble:
                                        (SEQ ID NO: 7)
5' UUCGUACCGGGUAGGUUGGCUUGCACAUAGAACGUGUCA 3'
```

Before each treatment, S76.T and the scramble aptamers underwent denaturation-renaturation using the following protocol: 85° C. for 5 minutes, cool down on ice for 2 minutes, and warm up to 37° C.

Tandem Protein Systematic Evolution of Ligands by Exponential Enrichment. Tandem protein Systematic Evolution of Ligands by Exponential Enrichment (SELEX) consists in the two separate in vitro cycles of selection. The counter-selection/selection rounds were repeated for eight cycles for the first round of selection following by two cycles for the second selection.

The starting DNA library of the first selection contains $10^{15}$ different random sequences with 2'-Fluoro-Pyrimidine (2'-F-Py) modification (TriLink Biotechnologies, San Diego, CA). The DNA library was composed by a random internal region of 40 base pairs flanked by two constant regions at 5' and 3' ends for the amplification reaction. The DNA library was prepared as described (Lamberti et al., 2016, Fitzwater and Polisky, 1996). However, the starting RNA pool of the second cycle of selection was the 2'-F Py selected sequence S5.

His-tagged CD5L (Sino Biological Inc., Beijing, China) was used as target for the selection step and His-tagged VEGF-A (Abnova, Taiwan), His-tagged CD19 (Life Technologies, Carlsbad, CA) and 6-His Peptide tagged (BioLegend, San Diego, CA) for the counter-selection step.

To enhance the specificity of aptamers for target protein, the RNA pool was incubated with His-tagged counter-selection protein for 30 min (counter-selection step). The unbound sequences were incubated with the target protein CD5L (selection step) at room temperature. The RNA-protein complexes were recovered by incubation with Ni2+ NTA Magnetic Agarose Beads (Qiagen, Hilden, Germany) for 30 min The bound sequences were isolated by total RNA extraction using TRIzol Reagent (Life Technologies, Carlsbad, CA), reverse transcribed with M-MuLV Reverse Transcriptase (Roche, Indianapolis, IN) and amplified by PCR (1 min at 93° C., 1 min at 53° C. and 1 min at 72° C.) under high MgCl2 and dNTP concentrations to introduce random mutations into the sequences.

The DNA template was in vitro transcribed to RNA. Before each round of SELEX, 2'-F Py RNA pool was subjected to a denaturation-renaturation as described above. The binding buffer used was composed by 10 mM Tris HCl 7.5, 150 mM NaCl, 1 mM $MgCl_2$, 0.1% Triton.

To enhance the stringency, progressively the number of washings was increased and the RNA/protein molar ratio was reduced. The final pool was cloned using TOPO-TA (TOPO Cloning, Life Technologies, Carlsbad, CA) and transforming into *Escherichia coli*. The clones were isolated and sequenced (www.eurofinsdna.com). ClustalW2 software was used for sequences analysis and alignments and TreeVieX program was used to visualize phylogenetic tree. RNA structure software (version 5.1) was used to predict the secondary structures.

Microscale Thermophoresis (MTS). Four sequences from the first (S5, S72, S47 and S63) and second selection (S11, S23 and S76) were tested to determine the binding affinity by MTS.

A serial dilution of S5, S47, S63 and S72 was prepared in specific buffer composed by PBS pH 7.4, 1 mM of $MgCl_2$ and 0.05% Tween20. The highest concentration used was 18000 nM and the lowest 0.54 nM. 4 μl of each dilution step were mixed with 4 μl of the labeled molecule CD5L purified recombinant protein (Sino Biological Inc., Beijing, China) or VEGF scrambled protein used as negative control (R&D System) (constant concentration of 12.5 nM).

The four different aptamers were tested for binding for CD5L and VEGF protein. Table 2 shows the $K_D$ values.

Regarding the three sequences of the second selection, S11 and S23 sequences were incubated with constant concentration (1 nM) of labeled CD5L purified recombinant protein (Sino Biological Inc., Beijing, China) or labeled VEGF scrambled protein used as negative control (R&D System). S11 and S23 were diluted 1:1 (from 15000 to 0.05 nM) in binding buffer (pH 7.4, 1 mM $MgCl_2$, 0.1% Tween20). S76 sequence was diluted 1:1 in Tris-buffered saline (TBS) from 1000 nM to 0.03 nM. S76.T was labeled with Cy5 and the concentration was kept constant at 2 nM. CD5L was diluted from 2000 nM to 0.06 nM in 50 mM Tris-HCl pH 7.8, 150 mM NaCl, 0.05% Tween20. 5 μl of each dilution step were mixed with 5 μl of the labeled CD5L or VEGF. The final reaction mixture contained a respective amount of aptamer sequences and constant 1 nM labeled CD5L or VEGF.

For Cy5 labeled S76.T, a serial dilution of CD5L was prepared in the buffer composed by 50 mM Tris-HCl pH7.8, 150 mM NaCl, 10 mM $MgCl_2$, 0.05 Tween-20. The highest concentration of CD5L was 2000 nM and the lowest 0.06 nM. 4 μl of each dilution step were mixed with 4 μl of the Cy5 labeled S76 truncated (4 nM stock). The final reaction mixture, which was filled in standard capillaries, contained a respective amount of CD5L (max. conc. 1000 nM, min conc. 0.03 nM) and constant 2 nM labeled S76 truncated MST measurement was obtained using Monolith NT.115 (NanoTemper Technologies GmbH, Munich, Germany) with standard capillaries. $K_D$ was determined as described by (Stoltenburg et al., 2015).

Statistical Analyses. Kaplan-Meier survival curves were generated and compared with the use of a log-rank statistic to assess the effect of tumor vascular CD5L expression on human overall survival, as well as to determine survival in our Tie2-cre; PPAR-γ KO mice model. For the animal experiments in FIGS. 4A-4G and 5E-5J, mice were assigned per treatment group. This sample size gave 80% power to detect a 50% reduction in tumor weight with a 95% confidence interval. Tumor weights and the number of tumor nodules for each group were compared using either the Student's t-test (for comparisons of two groups) if the distribution was normal, or Mann-Whitney if the distribution was non-normal. A P-value of less than 0.05 were deemed statistically significant. All statistical tests were two-sided and were performed using either SPSS version 12 for Windows statistical software (SPSS, Inc., Chicago, IL) or GraphPad Prism 7 for Windows (GraphPad Software, La Jolla, CA).

Example 2—Adaptive Genomic Changes in Tumor Endothelial Cells

To identify possible targets involved in adaptive resistance, the syngeneic ID8 ovarian cancer mouse model was used. Mice were treated with the B20 antibody and tumors were obtained at time points demonstrating both sensitivity and resistance (FIG. 1A). Endothelial cells were then isolated from sensitive and resistant tumor samples and gene expression profiling was performed using isolated mRNA. A large number of genes displayed differential expression between the endothelial cells from sensitive versus resistant tumors, with CD5L demonstrating the largest difference of 28.48 fold higher in the resistant endothelial cells (FIG. 1B). A subset of genes was then selected from the array and subjected to qRT-PCR to confirm the observed increase in CD5L expression in the resistant setting (FIG. 1C). Using immunohistochemistry, CD5L protein expression was found to be significantly higher in the endothelial cells from resistant tumors compared to those from sensitive tumors (FIG. 1D).

Figure 1E:
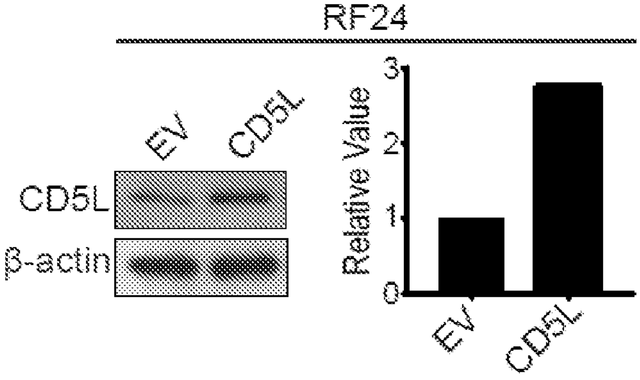
Figure 1F:
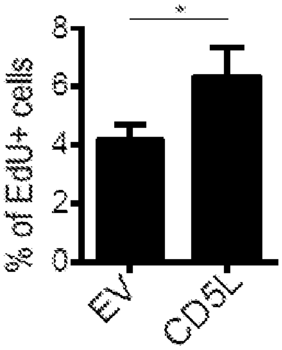
Figure 1G:
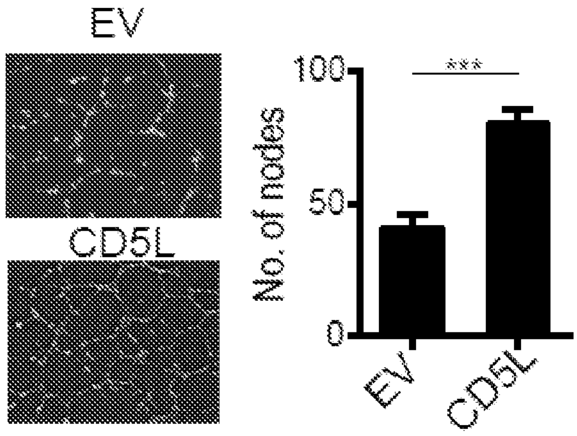
Figure 1H:
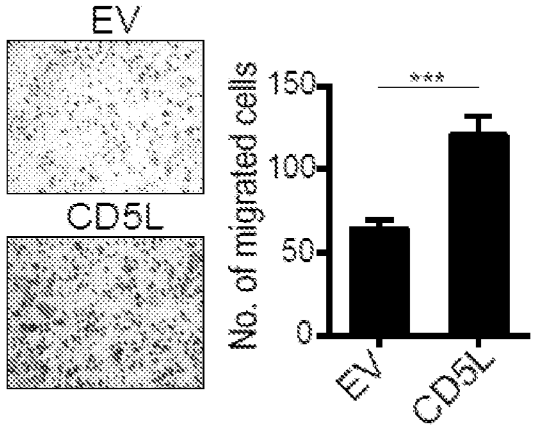
Figure 1I:
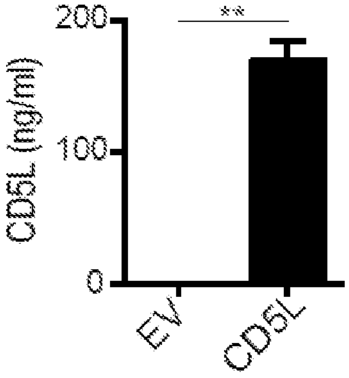
Figure 1J:
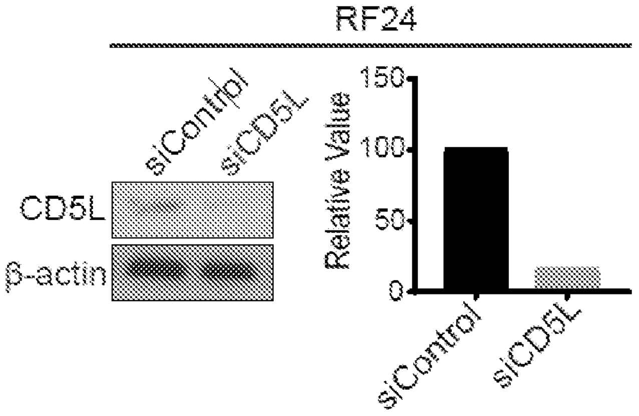
Figure 1K:
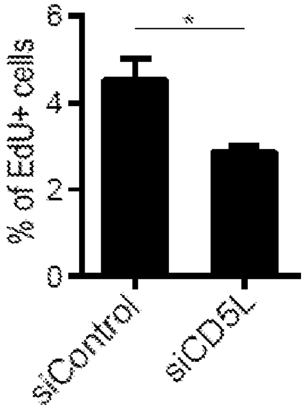
Figure 1L:
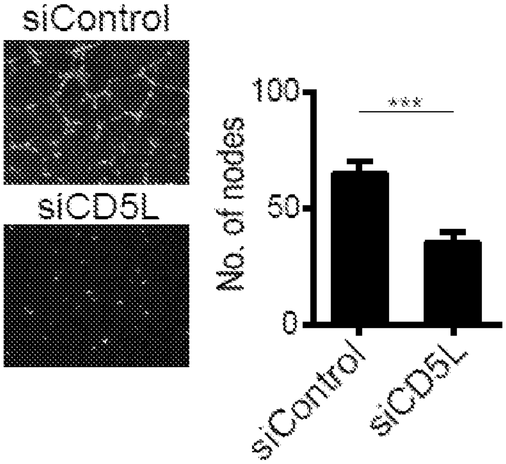
Figure 1M:
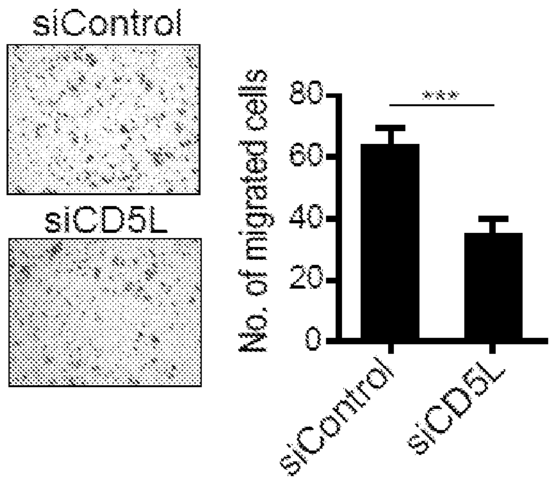

Next, the biological effects of CD5L upregulation in tumor endothelial cells was examined. To determine the function of CD5L in tumor angiogenesis, CD5L overexpressing RF24 cells were generated (FIG. 1E). These cells displayed elevated proliferation, increased tube formation capacity, and increased cell migration compared to controls (FIGS. 1F and 1H). Consistent with CD5L being a primarily secreted protein, the concentration of CD5L in the media from RF24 cells overexpressing CD5L was shown to be significantly higher than media from control RF24 cells (empty vector) (FIG. 1I). To confirm that the overexpression of CD5L was the primary source of these observed effects, control RF24 cells were treated with CD5L siRNA. More than a 90% knockdown of CD5L protein levels was seen within 72 hours compared with a non-targeting siRNA (FIG. 1J). Notably, cells treated with CD5L siRNA showed significantly reduced proliferation, tube formation capacity, and cell migration compared to cells treated with control siRNA (FIGS. 1K and 1M).

Example 3—CD5L is Upregulated Through Hypoxia-Induced PPAR-γ Overexpression

Figure 2A:
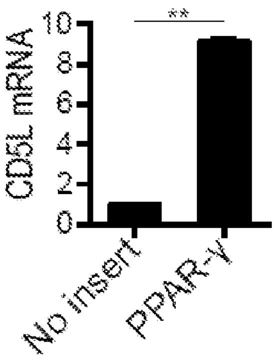
FIGS. 2A-2N. CD5L is Upregulated Through Hypoxia-Induced PPAR-γ Overexpression.
Figure 2B:
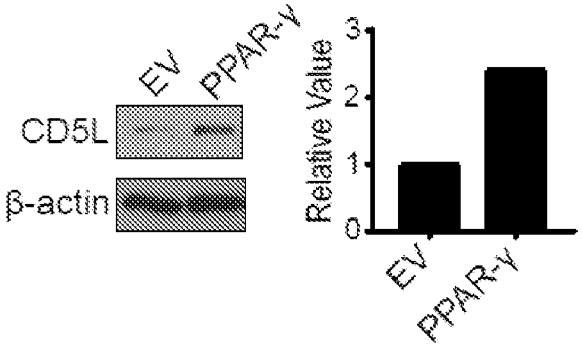
Figure 2C:
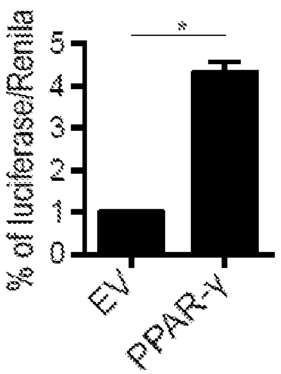
(FIG. 2C) CD5L promoter construct activation using either RF24 endothelial cells containing PPAR-γ overexpressing plasmid versus (EV).
Figure 2D:
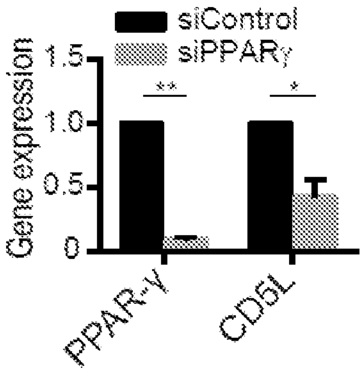
(FIGS. 2D&2E) PPAR-γ and CD5L mRNA (FIG. 2D) and protein (FIG. 2E) expression in RF24 endothelial cells treated with siPPAR-γ versus siControl.
Figure 2E:
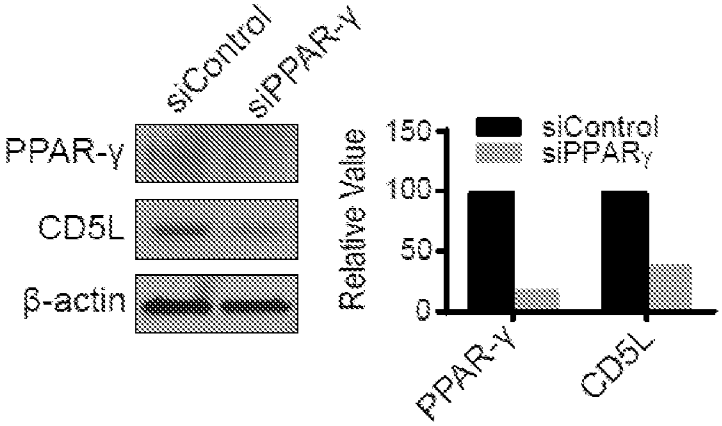
Figure 2F:
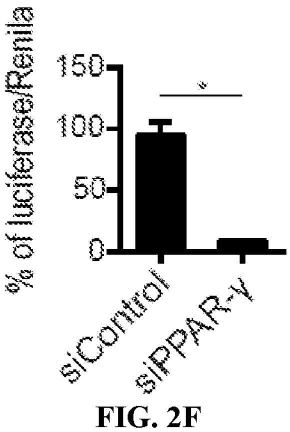
(FIG. 2F) CD5L promoter construct activation using RF24 endothelial cells treated with siPPAR-γ versus siControl.
Figure 2G:
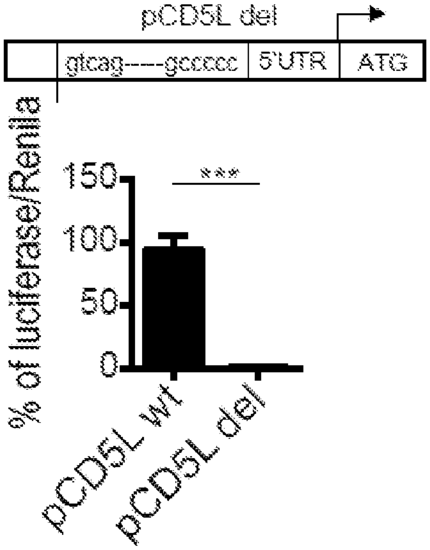
(FIG. 2G) Luciferase expression in RF24 endothelial cells after co-transfection of PPAR-γ overexpressing plasmid and CD5L promoter construct harboring mutated PPAR-γ binding site.

To determine possible mechanisms of CD5L elevation in tumor endothelial cells, regulation of CD5L gene transcription was examined. Upon analysis of the CD5L promoter sequence, a putative binding site for the transcription factor PPAR-γ was identified (FIG. 8). To test whether PPAR-γ may serve as an upstream regulator of CD5L, PPAR-γ was ectopically expressed in RF24 endothelial cells. Compared with controls, endothelial cells with elevated PPAR-γ demonstrated a significant increase in both CD5L mRNA and protein (FIGS. 2A and 2B). Additionally, a CD5L promoter construct (pCD5L WT) was generated and a significant increase in luciferase activity was found when transfected into PPAR-γ overexpressing RF24 cells compared to wild type RF24 cells (FIG. 2C). To further prove that PPAR-γ expression was responsible for the observed increases in CD5L expression and promoter activity, wild-type RF24 cells were treated with PPAR-γ siRNA. Cells that were treated with PPAR-γ siRNA showed a significant reduction in both CD5L mRNA and protein (FIGS. 2D and 2E), as well as decreased luciferase activity from the CD5L promoter construct (FIG. 2F). Next, the PPAR-γ binding site was deleted from the CD5L promoter construct (pCD5L del) to determine whether the CD5L increase observed was due to PPAR-γ specific binding. After co-transfecting RF24 cells with the PPAR-γ expression plasmid and either pCD5L WT or pCD5L del, it was found that the mutated PPAR-γ binding site resulted in significantly reduced luciferase activity compared to the non-mutated promoter, indicating that PPAR-γ directly regulates CD5L expression (FIG. 2G).

Figure 2H:
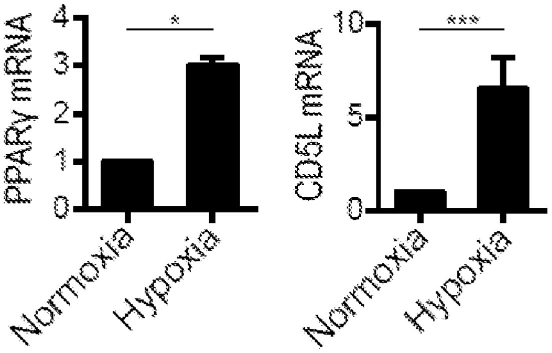
(FIGS. 2H&2I) PPAR-γ and CD5L mRNA (FIG. 2H) and protein (FIG. 2I) expression in RF24 endothelial cells cultured in hypoxic or normoxic conditions.
Figure 2I:
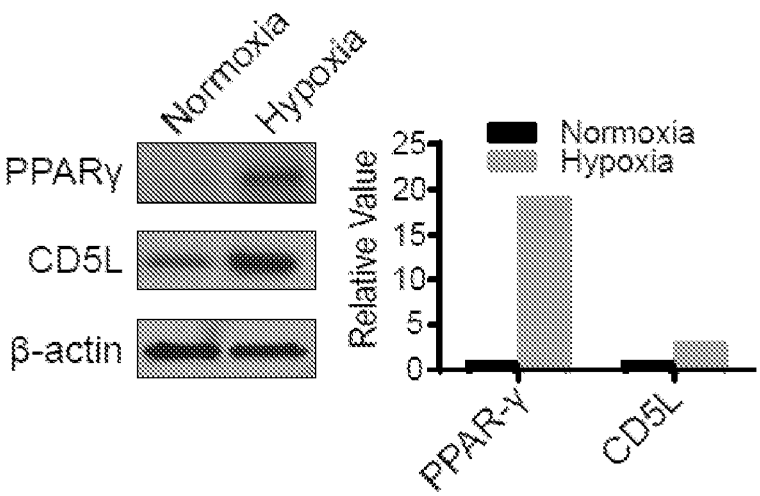
Figure 2J:
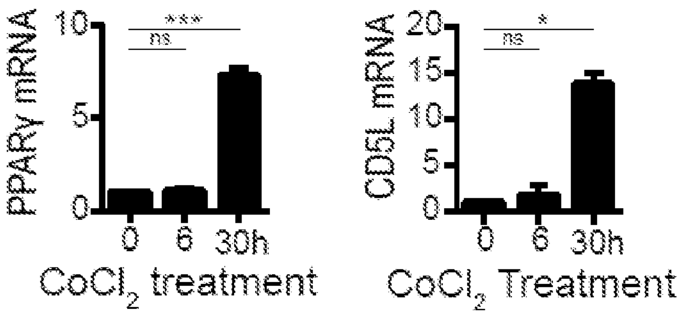
(FIGS. 2J&2K) PPAR-γ and CD5L mRNA (FIG. 2J) and protein (FIG. 2K) expression in RF24 endothelial cells treated for 6 and 30 hours with cobalt chloride (HIF1α stabilizer).
Figure 2K:
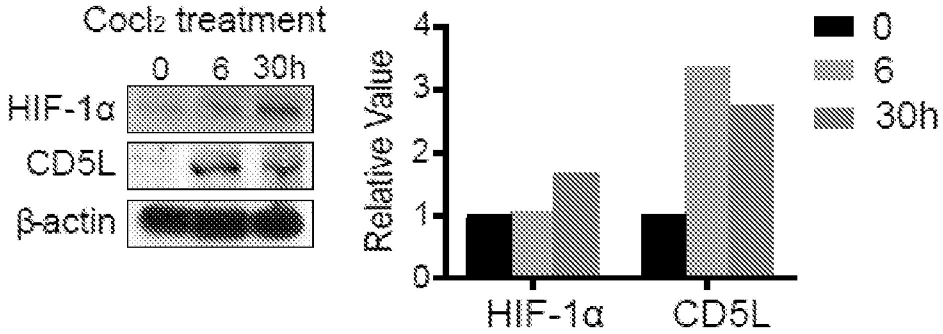
Figure 2L:
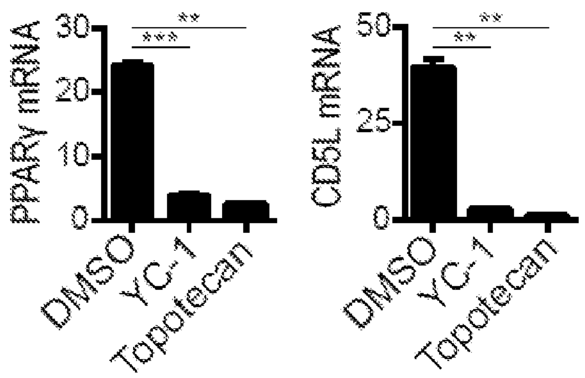
(FIG. 2L) PPAR-γ and CD5L mRNA expression in RF24 endothelial cells treated with YC-1 or topotecan under hypoxic conditions.
Figure 2M:
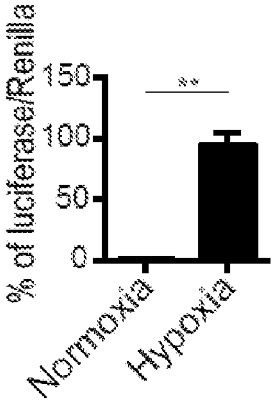
(FIG. 2M) CD5L WT promoter construct activation in RF24 endothelial cells cultured in hypoxic and normoxic conditions.
Figure 2N:
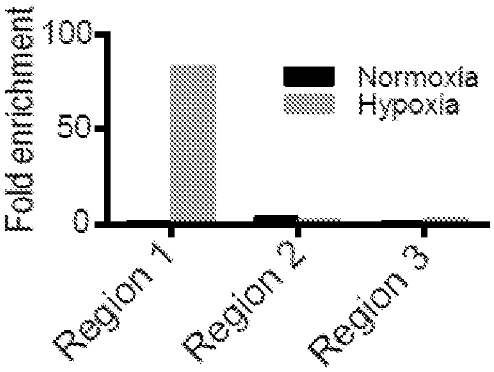
Figure 9:
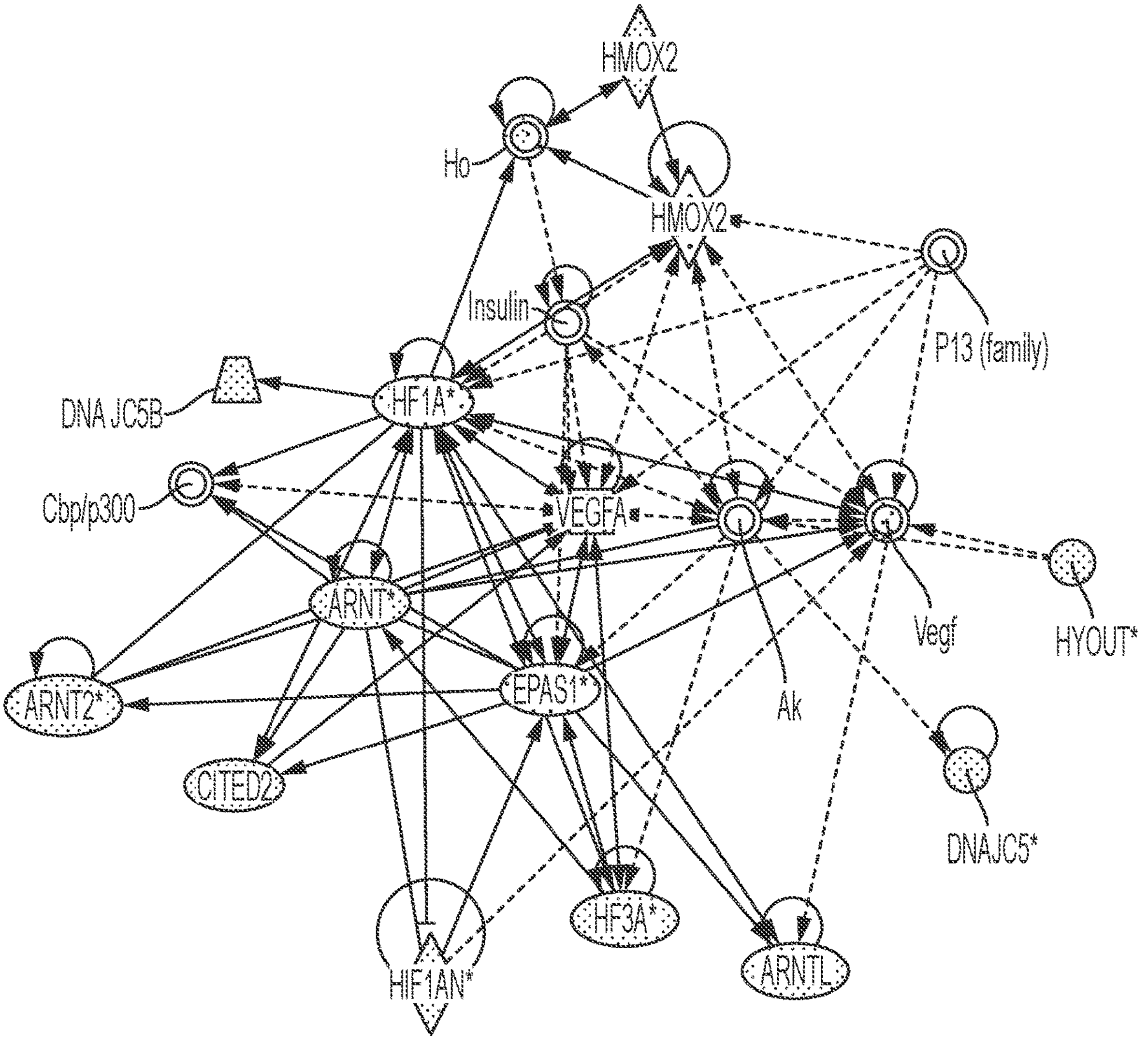
FIG. 9. Ingenuity Pathway Analysis (IPA) of AVA Resistant Mouse Tumor Endothelial Cells. Resistance to anti-VEGF therapy is associated with increased hypoxia signaling. IPA analysis performed on gene expression profile presented in FIG. 1B.

Next, whether any other factors upstream of PPAR-γ played a role in the upregulation of CD5L was sought to be determined. Using the initial gene expression dataset generated from anti-VEGF resistant endothelial cells, an ingenuity pathway analysis (IPA) was performed and a close correlation with hypoxia signaling proteins (HIF1A, EPAS1, ARNT) was found (FIG. 9). To confirm this relationship, WT RF24 cells were grown under hypoxic and normoxic conditions and a significant increase in both PPAR-γ and CD5L mRNA and protein levels was found in cells grown under hypoxic compared to normoxic conditions (FIGS. 2H and 2I). Extending this finding further, RF24 cells were incubated with a HIF1A stabilizing compound (cobalt chloride—$CoCl_2$) for 6 and 30 hours under normoxic conditions. Both PPAR-γ and CD5L mRNA expression was significantly higher after 30 hours of $CoCl_2$ incubation compared to 6 hours as well as no treatment, further demonstrating that hypoxia-like conditions lead to the upregulation of PPAR-γ and CD5L (FIG. 2J). In addition, HIF1A and CD5L protein expression were also increased at longer incubation times of $CoCl_2$, as expected (FIG. 2K). To determine whether HIF1A blockade resulted in the opposite effect on PPAR-γ and CD5L, two known HIF1A inhibitors, YC-1 and topotecan, were employed. After treatment of WT RF24 cells with either YC-1 or topotecan, a significant decrease in both PPAR-γ and CD5L mRNA expression was found compared to DMSO control (FIG. 2L). Furthermore, CD5L promoter activity (pCD5L WT) was significantly increased when exposed to hypoxic versus normoxic conditions (FIG. 2M). Lastly, chromatin immunoprecipitation (ChIP) analysis of the CD5L promoter was performed using an anti-PPAR-γ antibody under hypoxic and normoxic conditions. The PPAR-γ binding site (located in region 1 of the CD5L promoter) had a significantly higher fold-enrichment for PPAR-γ under hypoxic compared to normoxic conditions (FIG. 2N). Moreover, the selectivity of PPAR-γ for the specific promoter sequence in region 1 was identified, as there was only minimal binding in regions 2 or 3 under normoxic or hypoxic conditions.

Example 4—Exogenous CD5L Increases PI3K/AKT Signaling in Endothelial Cells

Figure 3A:
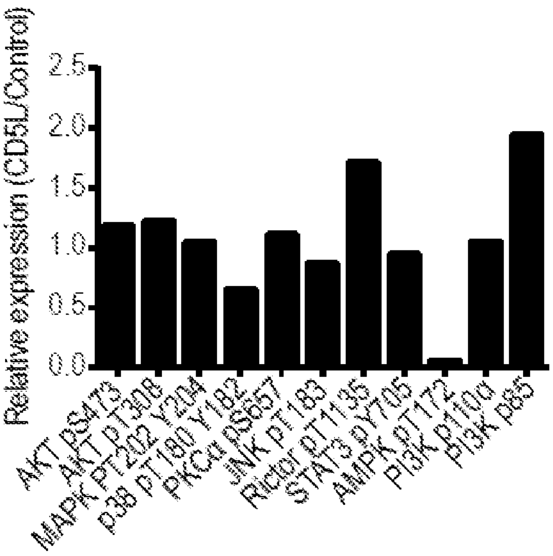
FIGS. 3A-3J. Exogenous CD5L Treatment of RF24 Endothelial Cells Results in Upregulation of PI3K/AKT Signaling.
Figure 3B:
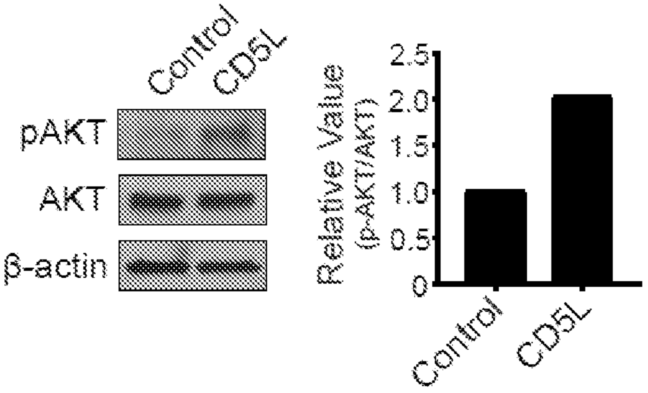
Figure 3C:
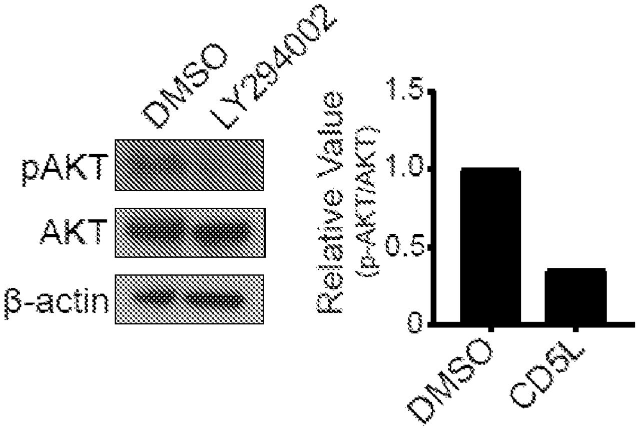
Figure 3D:
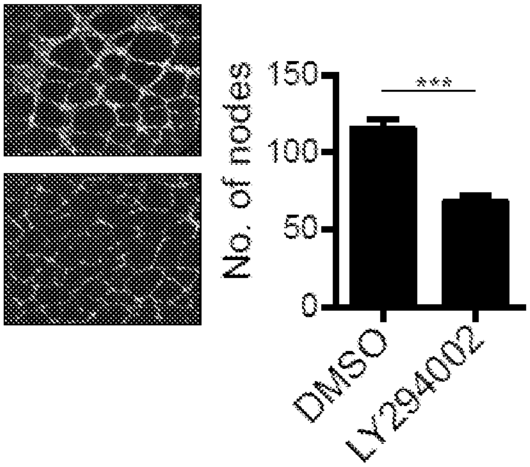
Figure 3E:
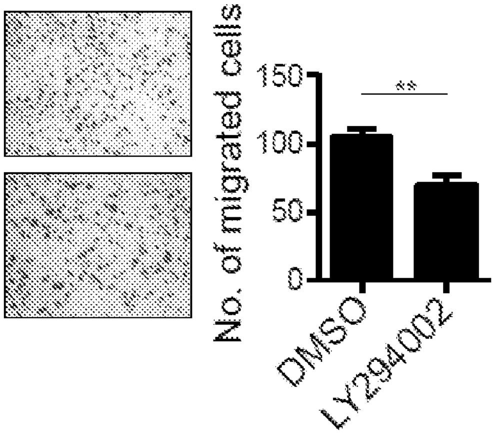
Figures 10A, 10B:
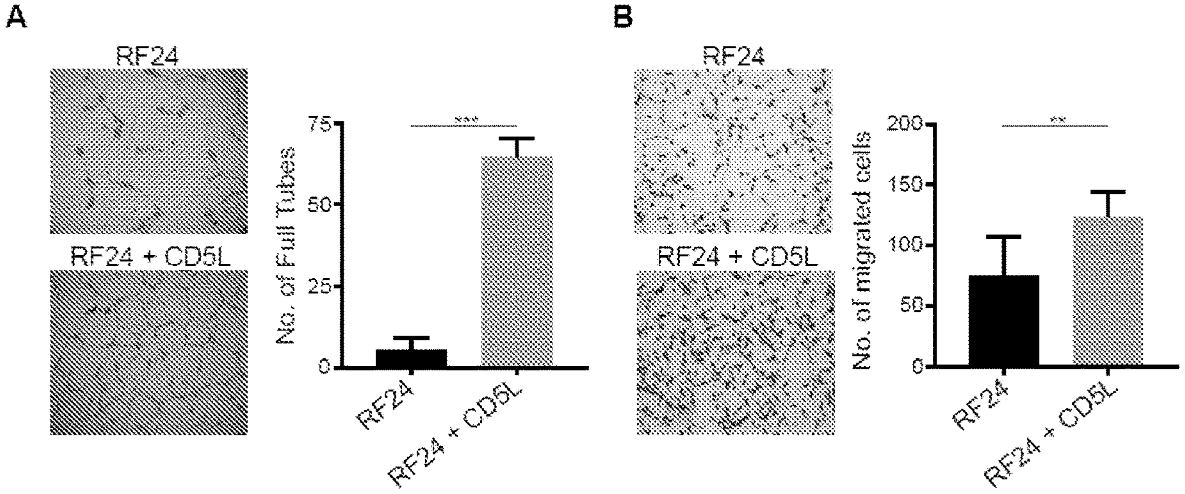
FIGS. 10A-10B. Effect of Exogenous CD5L Protein Treatment on RF24 Endothelial Cells. Tube formation (FIG. 10A) and cell migration (FIG. 10B) of RF24 cells alone or after addition of 400 ng/ml CD5L protein. (P<0.01, *P<0.001). Bars represent mean±sd.

As CD5L is primarily a secreted protein shown to act in a paracrine fashion, RF24 endothelial cells were exogenously treated with CD5L to determine the downstream signaling effects. Reverse phase protein array (RPPA) analyses of both CD5L-treated and untreated RF24 endothelial cells were performed, and the CD5L-treated cells showed activation of PI3K/AKT signaling (FIG. 3A). To validate these results, the protein levels of AKT and phosho-AKT in CD5L-treated RF24 cells were measured compared with untreated controls. The RF24 cells, which were pre-treated with CD5L, had increased expression of p-AKT compared with the untreated cells (FIG. 3B). Furthermore, addition of the PI3K inhibitor LY294002 after CD5L pre-treatment mitigated these stimulating effects on p-AKT (FIG. 3C). Similarly, both tube formation and cell migration of RF24 cells increased significantly after CD5L treatment (FIGS. 10A-10B); however, both were significantly decreased with the co-addition of a PI3K inhibitor, confirming the key role of PI3K signaling in the downstream effects of CD5L binding (FIGS. 3D and 3E).

Figure 3F:
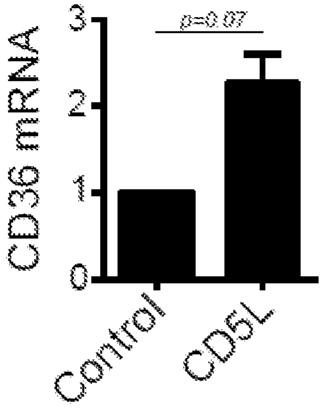
Figure 3G:
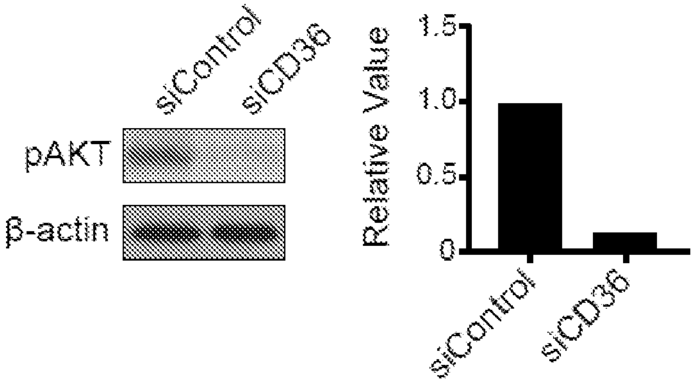
Figure 3H:
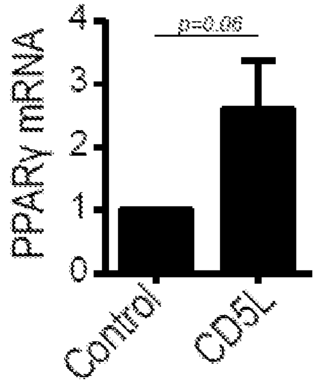
Figure 3I:
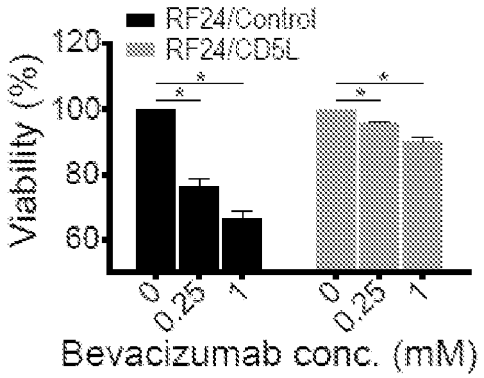
Figure 3J:
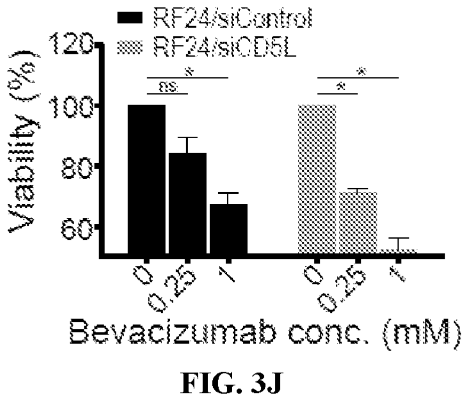

Next, as CD36 has been previously reported to be one of the major receptors for CD5L in macrophages, whether the effect of CD5L exogenous treatment on CD36 expression was sought to be determined. CD5L-treated RF24 cells had a significantly higher expression of CD36 than untreated RF24 cells (FIG. 3F), possibly through a positive feedback mechanism. To determine whether CD36 was implicated in the CD5L dependent upregulation of PI3K/AKT, RF24 cells were transfected with CD36 siRNA and again exogenously treated them with CD5L. Interestingly, the upregulation of p-AKT previously seen with exogenous CD5L treatment was negated under the conditions of CD36 receptor blockade (FIG. 3G). Also, exogenous CD5L treatment resulted in the same upregulation of PPAR-γ as previously demonstrated using the endogenous CD5L overexpressing construct (FIG. 3H). It is highly likely that the upregulation of the PI3K/AKT pathway is an integral component in the development of adaptive resistance to bevacizumab as RF24 cells exogenously treated with CD5L lost their sensitivity to bevacizumab compared to control cells (FIG. 3I). Moreover, treatment of RF24 cells with CD5L siRNA resulted in enhanced sensitivity to bevacizumab compared to siControl treated cells (FIG. 3J).

Example 5—Silencing of PPAR-γ Inhibits Angiogenesis and Tumor Growth

Figure 4A:
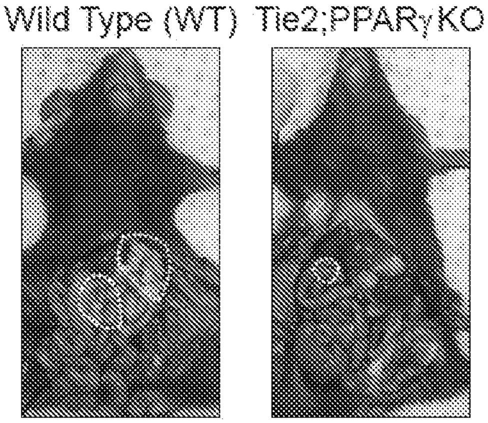
FIGS. 4A-4G. PPAR-γ Silencing Inhibits Tumor Growth and Angiogenesis in ID8 Xenograft Model.
Figure 4B:
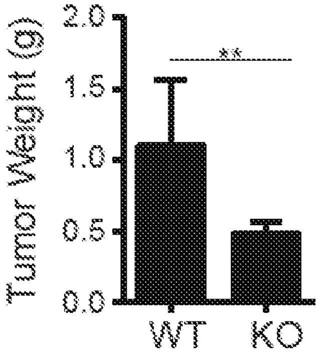
Figure 4C:
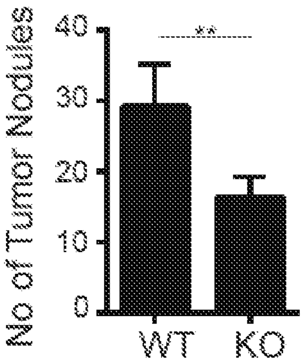
Figure 4D:
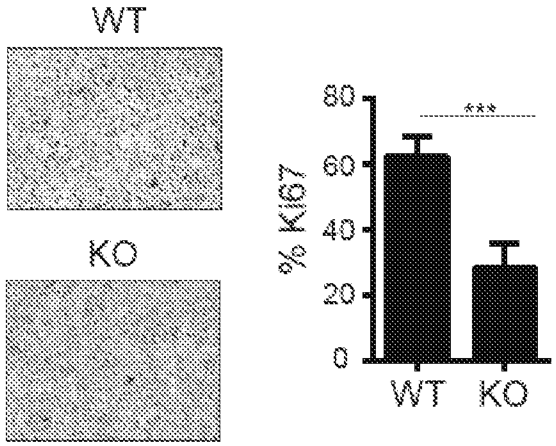
Figure 4E:
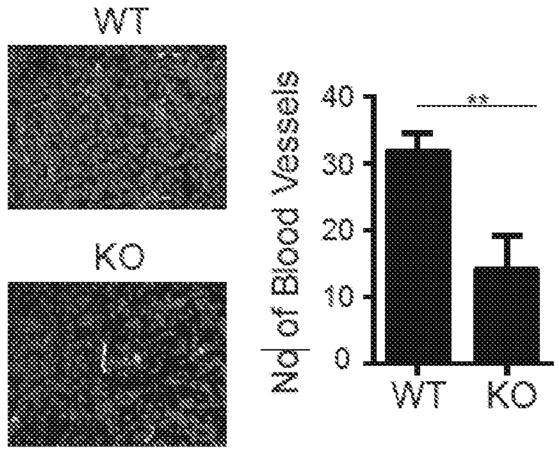
Figure 4F:
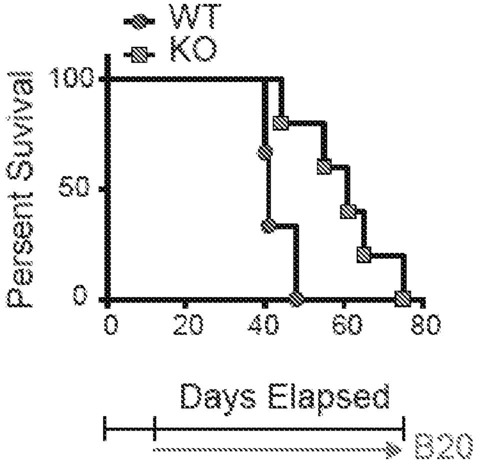
Figure 4G:
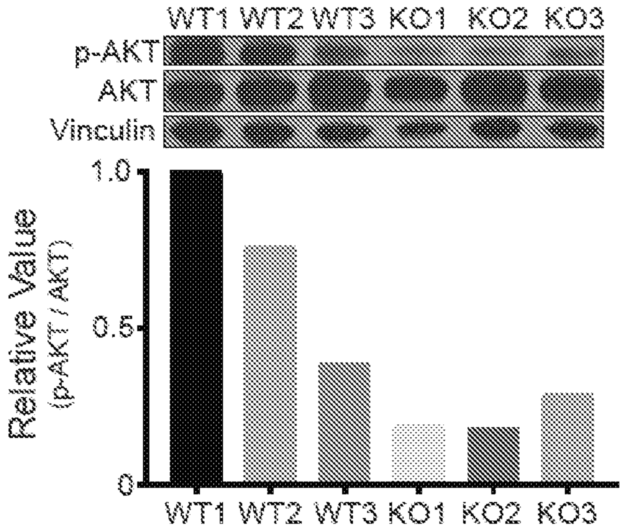

To further explore the function of PPAR-γ and CD5L in tumor endothelial cells, murine ID8 ovarian cancer cells were injected intraperitoneally into C57BL/6 mice containing an endothelial cell-specific PPAR-γ knockout as well as C57BL/6 WT mice (FIG. 4A) (Guignabert et al., 2009). A 50% reduction in tumor weight and number of tumor nodules in the PPAR-γ KO mice compared with WT mice was observed (FIGS. 4B, 4C, and 4D). Moreover, immunohistochemical (IHC) analysis of tumor tissues from PPAR-γ KO versus WT mice revealed a significant decrease in cell proliferation and microvessel density in the PPAR-γ KO mice (FIGS. 4E and 4F). Next, a survival analysis of PPAR-γ KO mice vs WT mice during concurrent anti-VEGF treatment was performed. Mice harboring a PPAR-γ KO had significantly improved survival while receiving anti-VEGF treatment compared to the WT mice. Consistent with the in vitro data, tumor samples from PPAR-γ KO mice had lower p-AKT expression compared to tumors from WT mice (FIG. 4G).

Example 6—S76.T, CD5L Aptamer, Blocks the Resistance to Anti-VEGF Therapy

Figure 11:
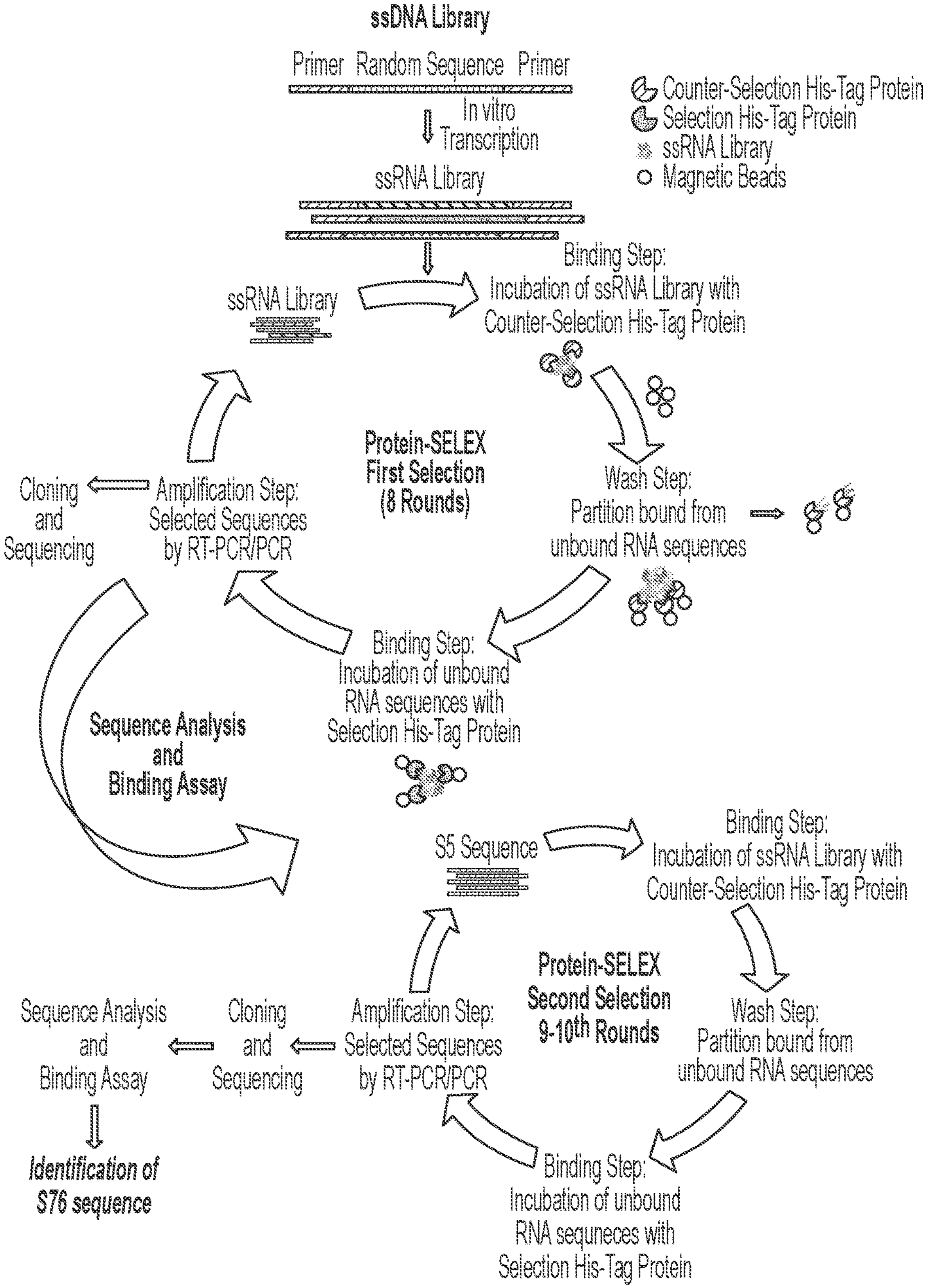
FIG. 11. Schematic Representation of Tandem Protein-SELEX. Schematic of S76.T selection by Tandem Protein SELEX FIGS. 12A-12C. Phylogenetic Tree of the First Round of Selection and Characterization of S5 Sequence.
Figure 12A:
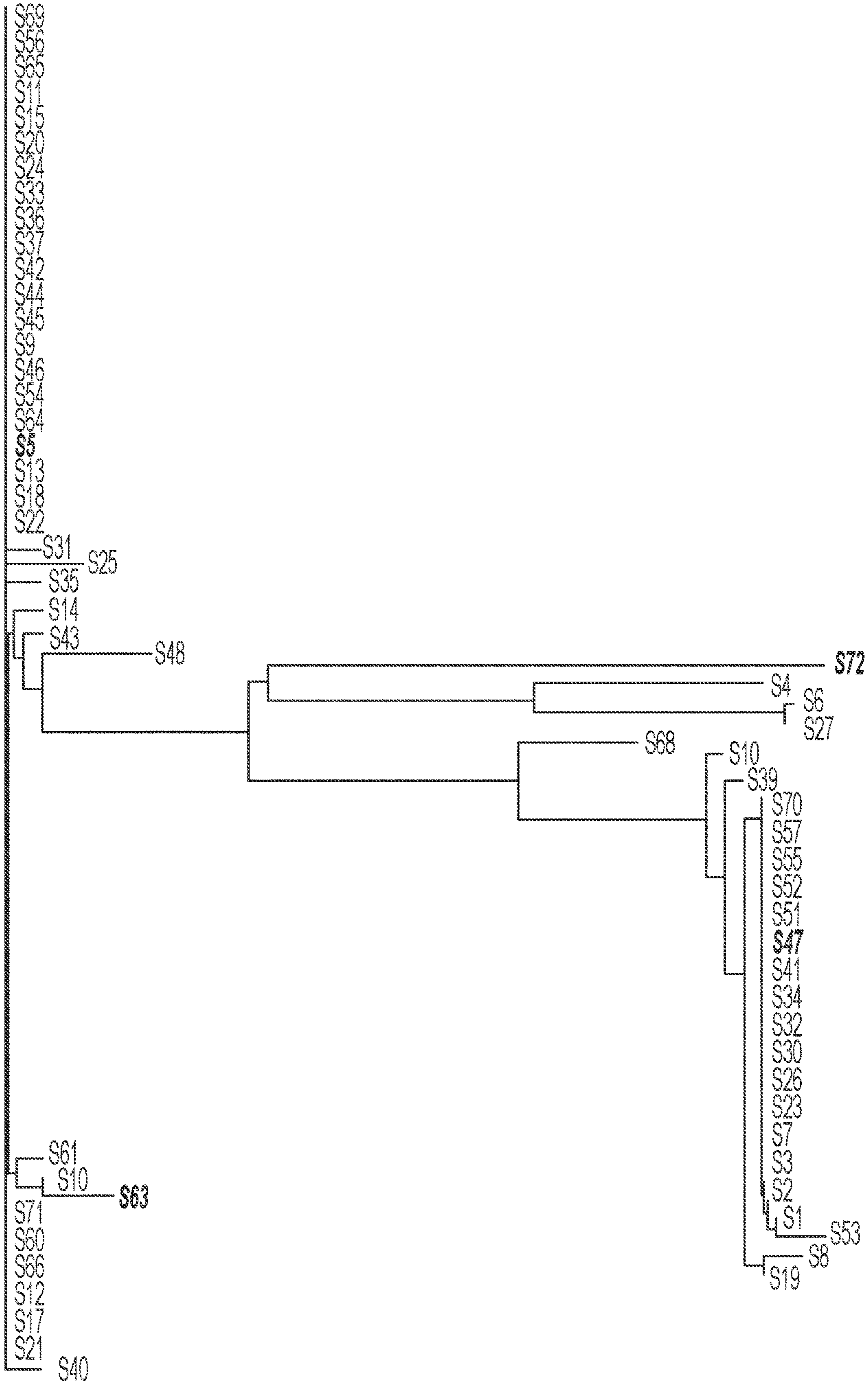
(FIG. 12A) Phylogenetic tree by using ClustalW2 software and visualized with TreeVieX program.
Figure 12B:
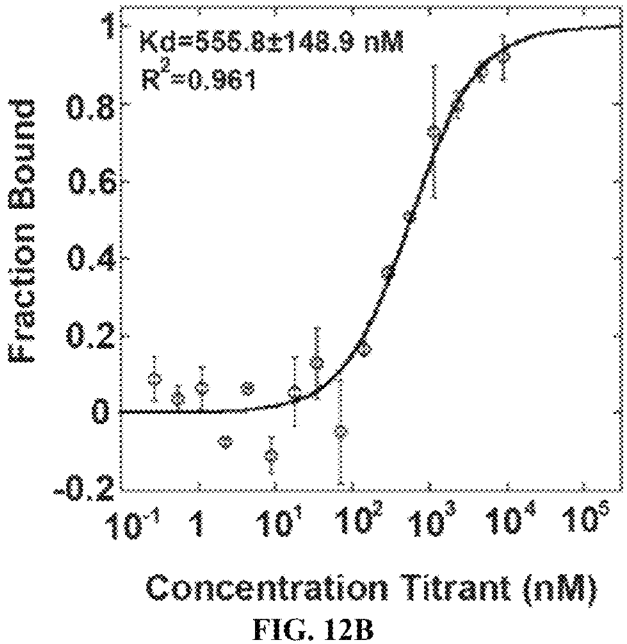
(FIG. 12B) S5 sequence binding curve obtained by Microscale thermophoresis (MTS).
Figure 12C:
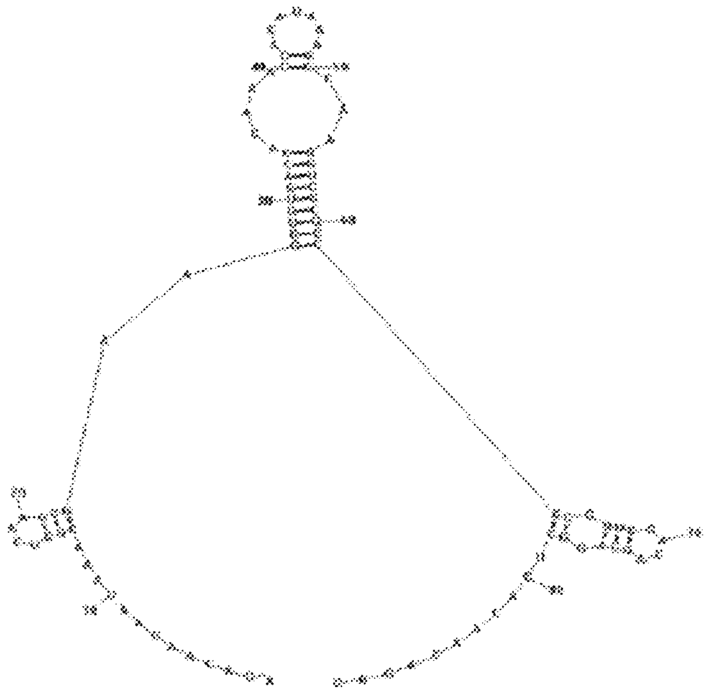
(FIG. 12C) Secondary structure prediction of S5 sequence (SEQ ID NO: 1) by using RNA structure version 5.1.

Considering the finding that anti-VEGF therapy resistance is mediated in part by overexpression of CD5L, the inventors aimed to develop an aptamer to specifically target CD5L and negate its downstream effects. S76.T is a 2'-fluoro pyrimidine RNA aptamer targeting CD5L. S76.T sequence was selected by two independent cycles of protein-SELEX (FIG. 11). During the first cycle of selection, four sequences (S5 (AGACAAGAAUAAACGCUCAAGCGAAGGU-GUGACCACAAACCACAUAAAGGCA AGGU-CGCGCCGCGUUCGACAGGAGGCUCACAACAGGC; SEQ ID NO: 1), S47, S63 and S72) were identified from the phylogenetic tree that could potentially bind CD5L (FIG. 12A). Among those sequences, the best aptamer for CD5L was the S5 sequence with a $K_D$ of 555.8±148.9 nM (FIG. 12B) determined by microscale thermophoresis. However, S63 and S72 sequences had no or weak binding for CD5L, while S47 was able to bind VEGF, used as negative control, and CD5L target protein (Table 3). The most stable predicted secondary structure of S5 full length, obtained by RNA structure prediction software, shows three hairpins like structures following by single strand ends (FIG. 12C).

Figure 13A:
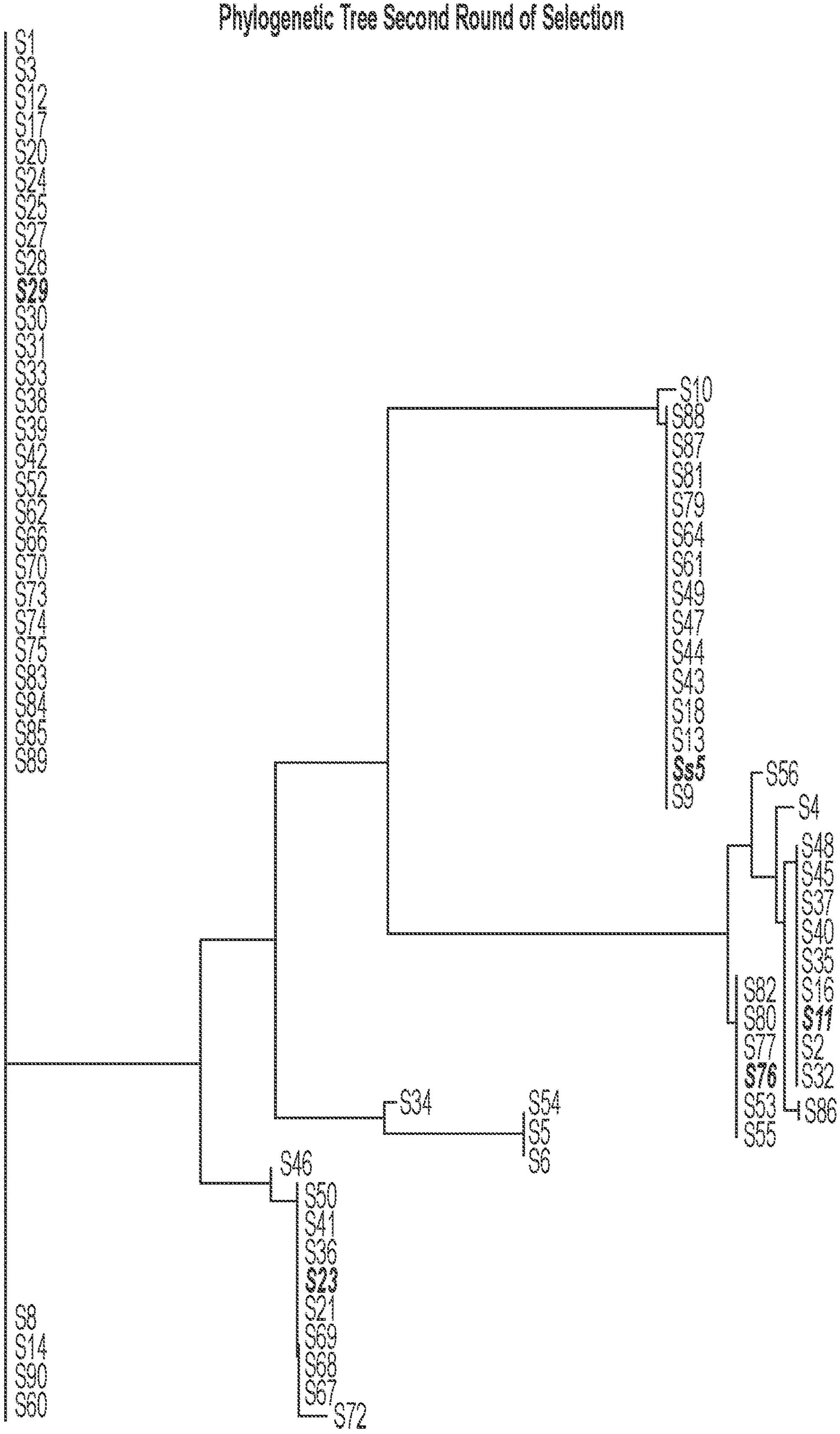
Figure 14A:
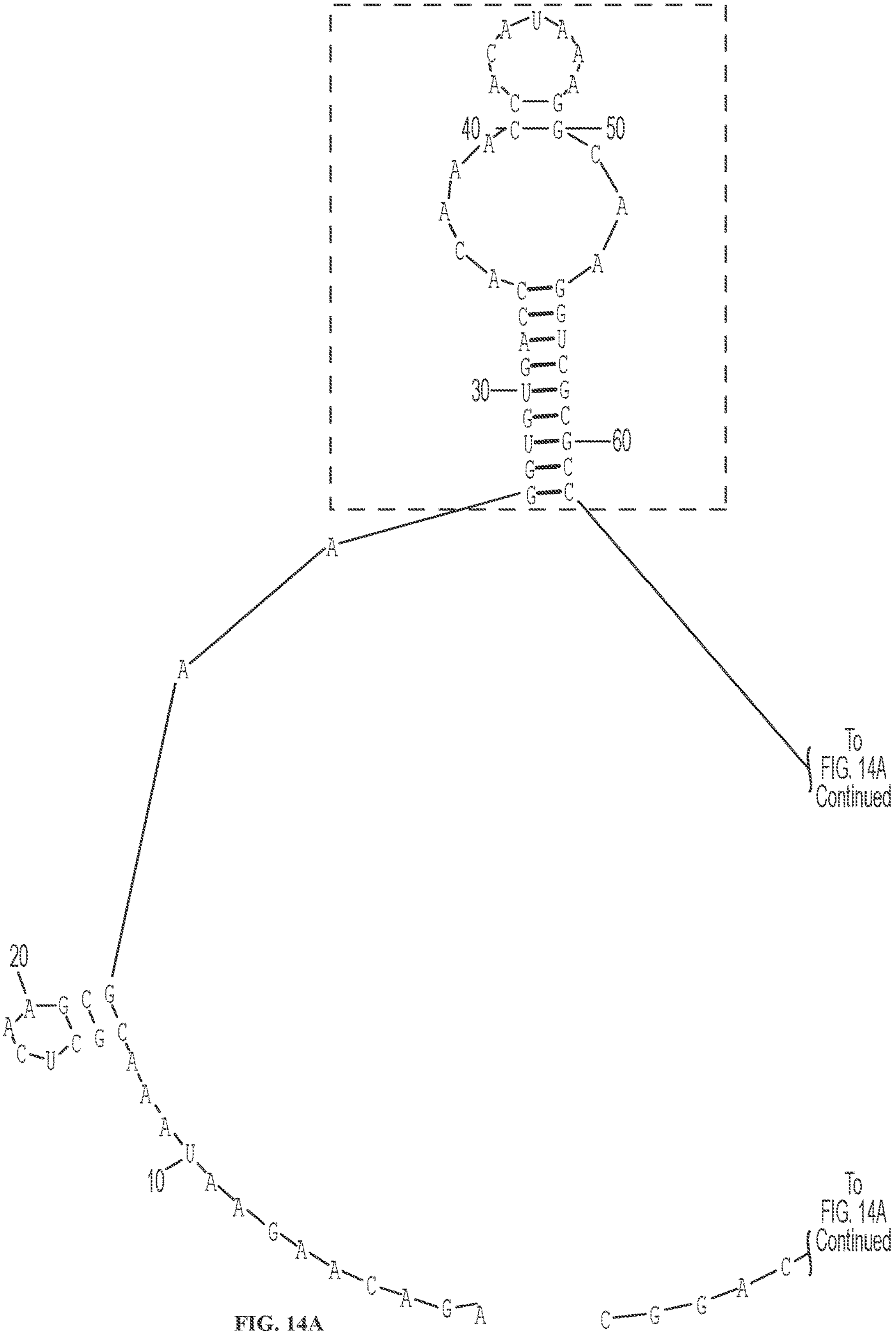
FIGS. 14A-14E. Identification of Binding Site for 511, S23, S29 and S76. Prediction of secondary structure of S5 (FIG. 14A; SEQ ID NO: 1), Si 1 (FIG. 14B; SEQ ID NO: 2), S23 (FIG. 14C; SEQ ID NO: 3), S29 (FIG. 14D; SEQ ID NO: 4), and S76 (FIG. 14E; SEQ ID NO: 5) sequences to identify the functional part of the aptamer involved in the recognition of CD5L target.
Figure 14A:
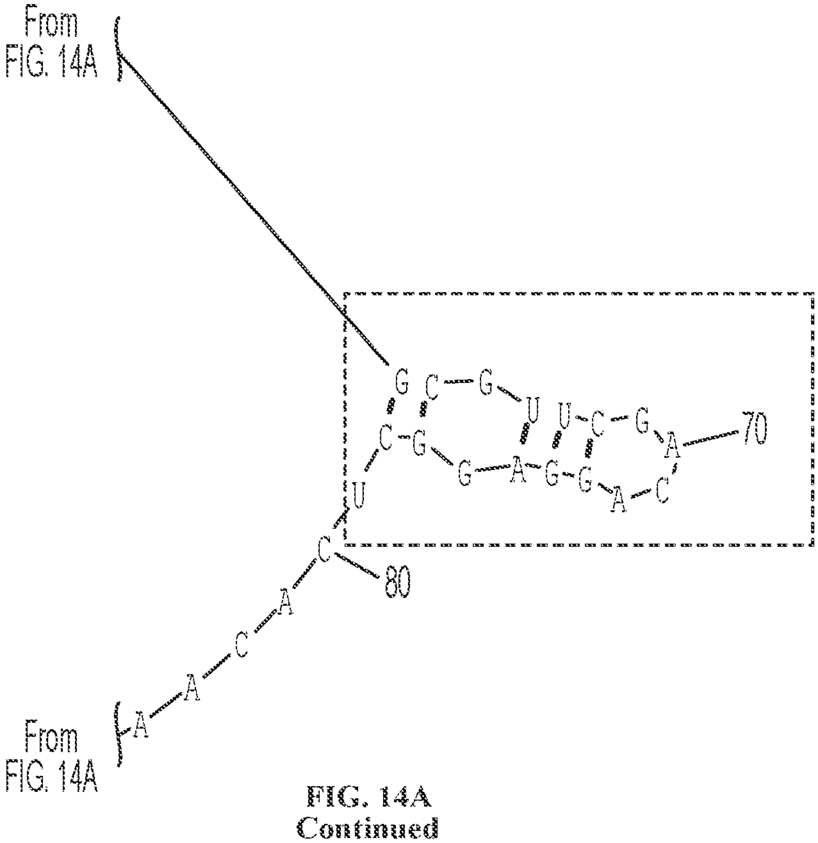
Figure 14B:
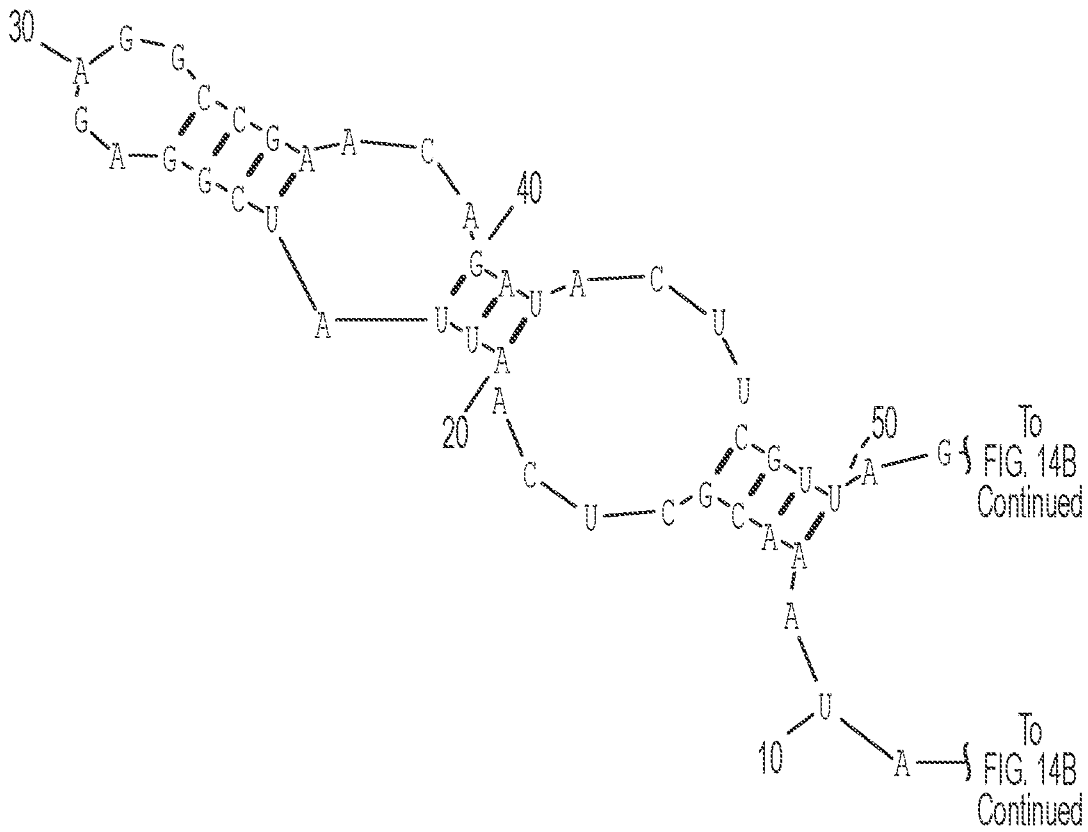
Figure 14B:
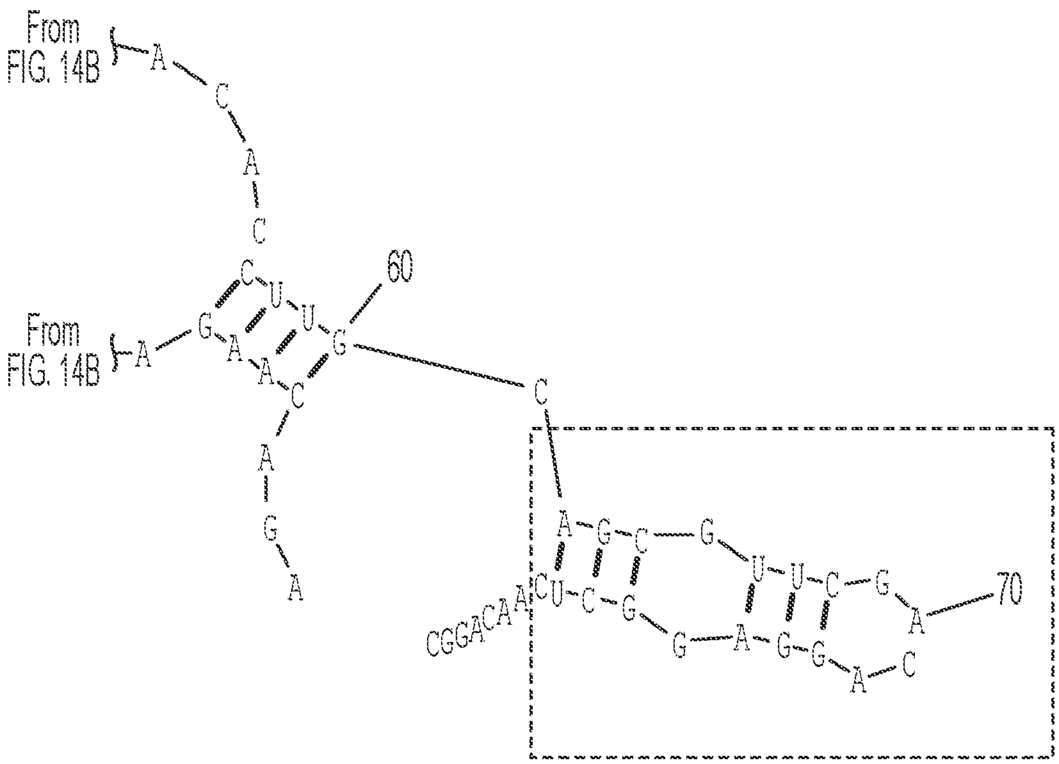
Figure 14C:
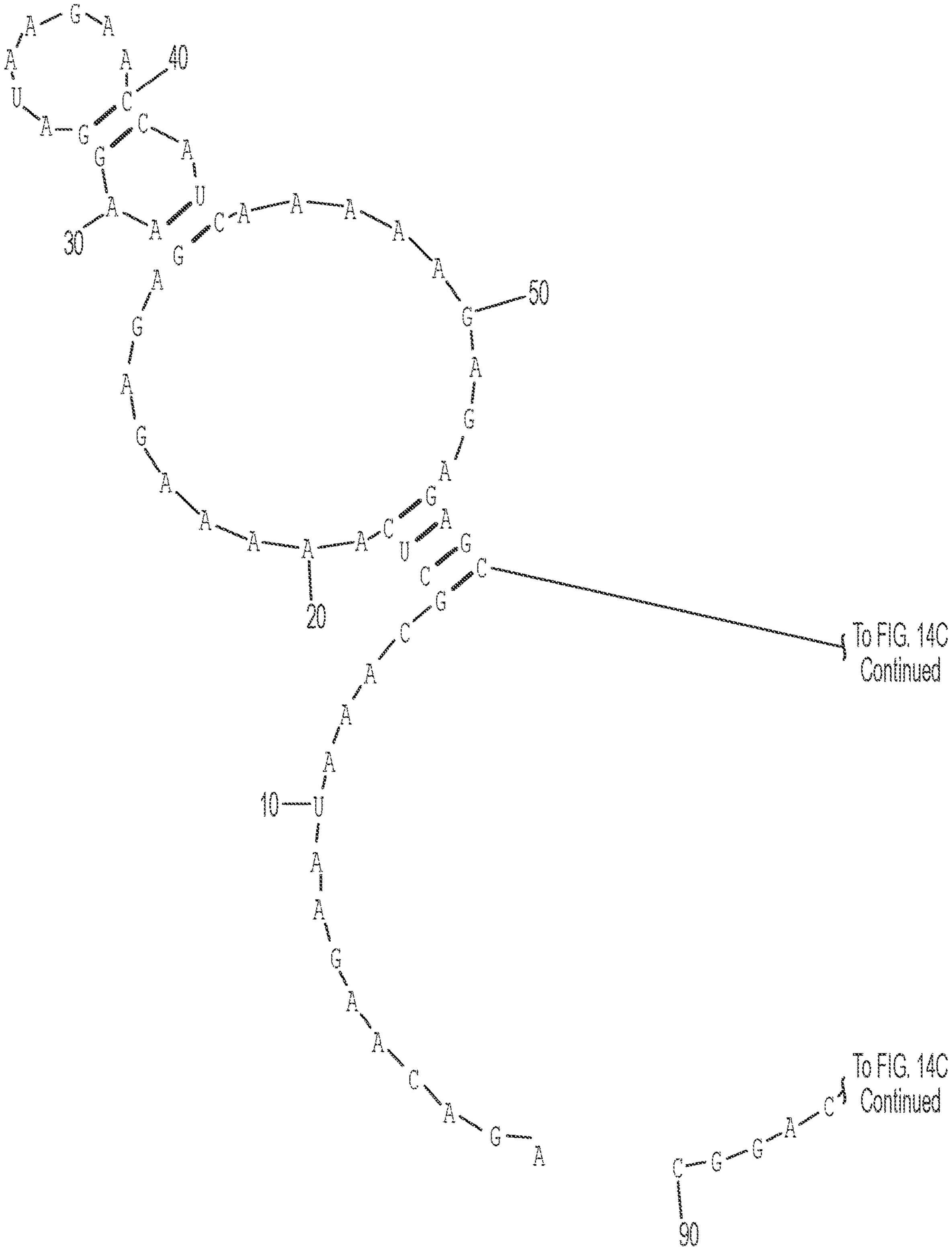
Figure 14C:
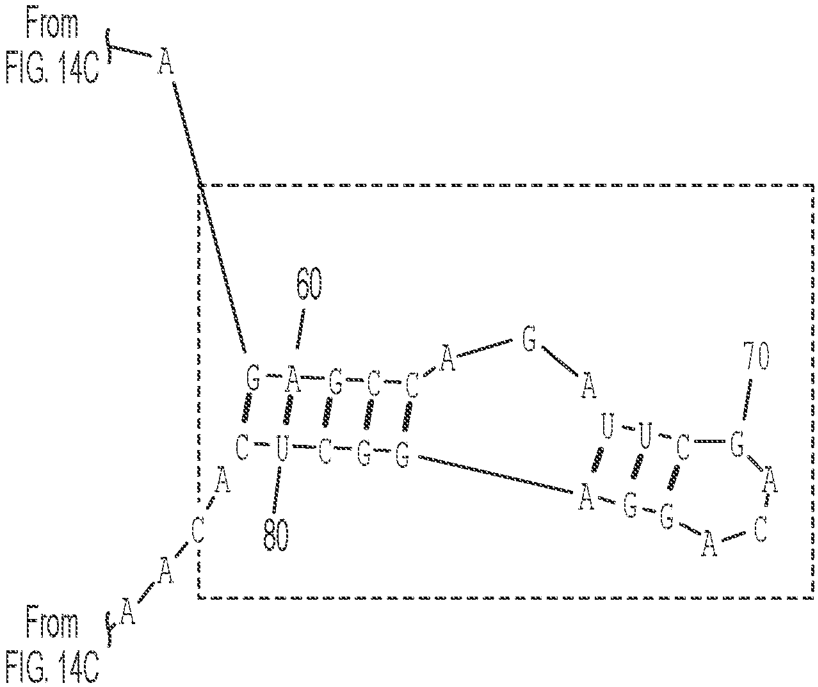
Figure 14D:
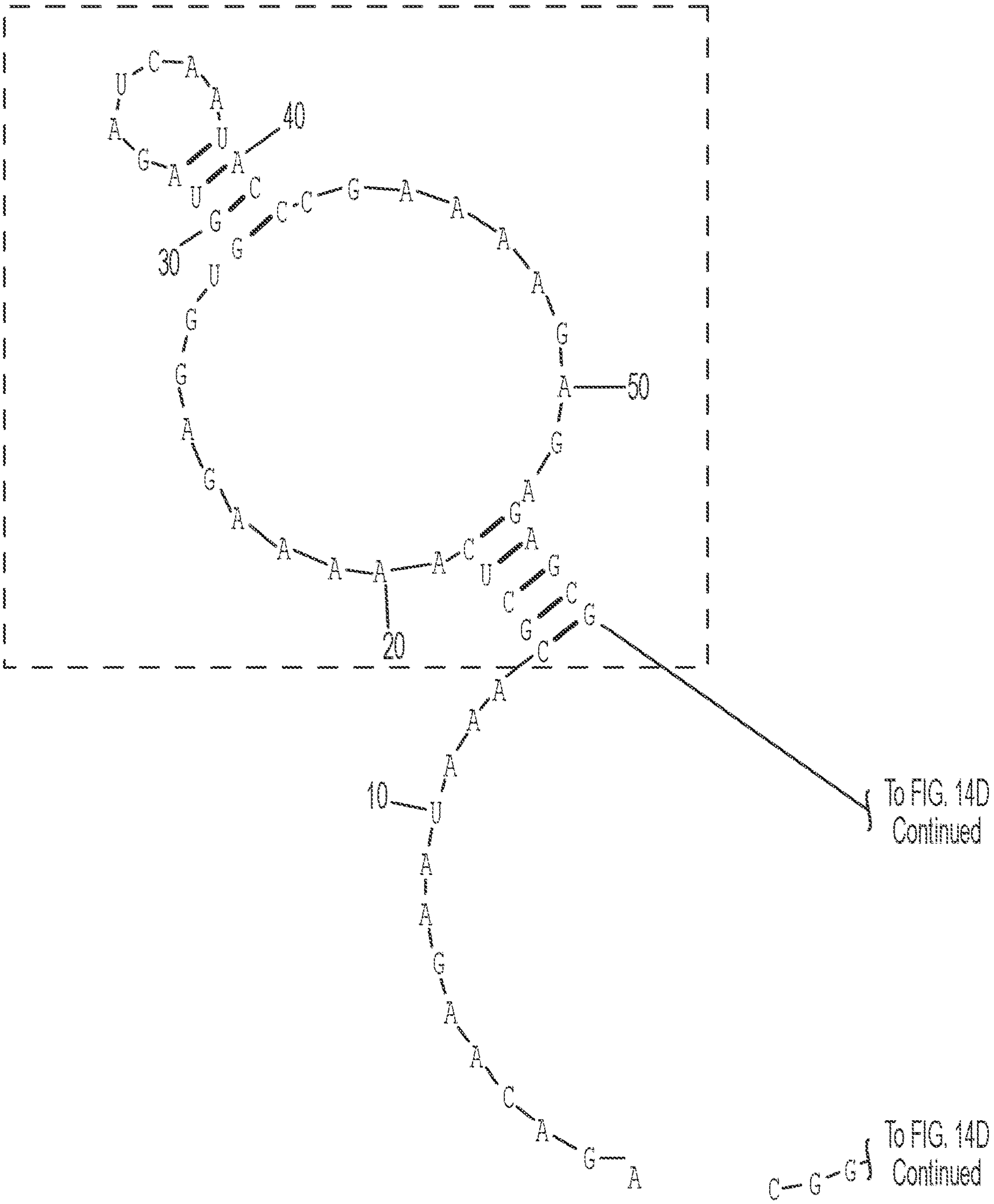
Figure 14D:
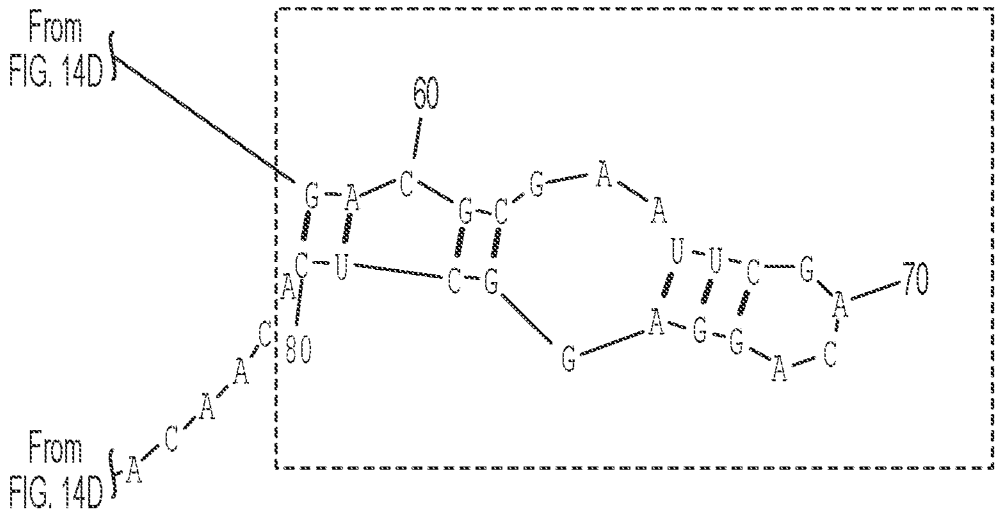
Figure 14E:
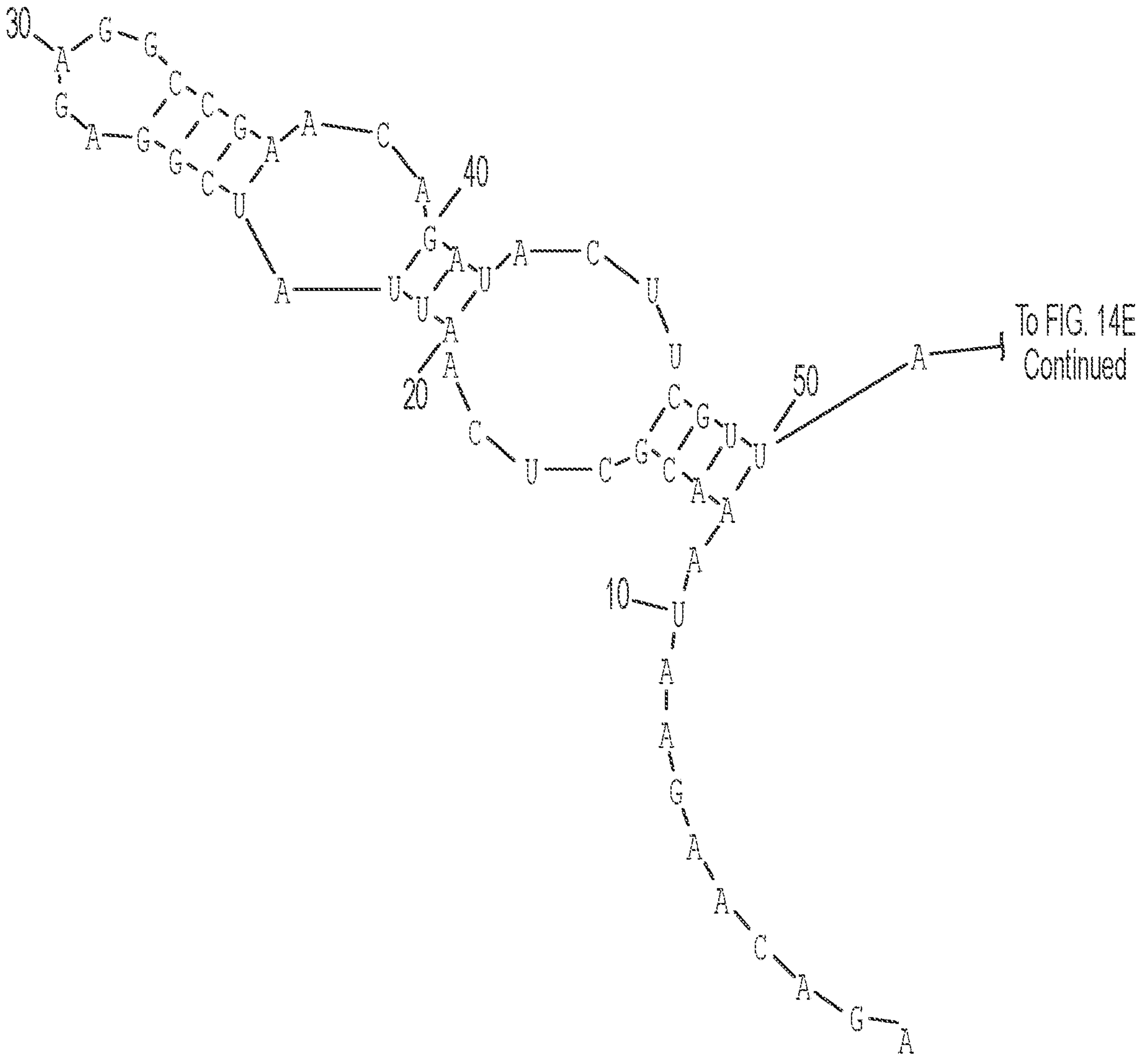
Figure 14E:
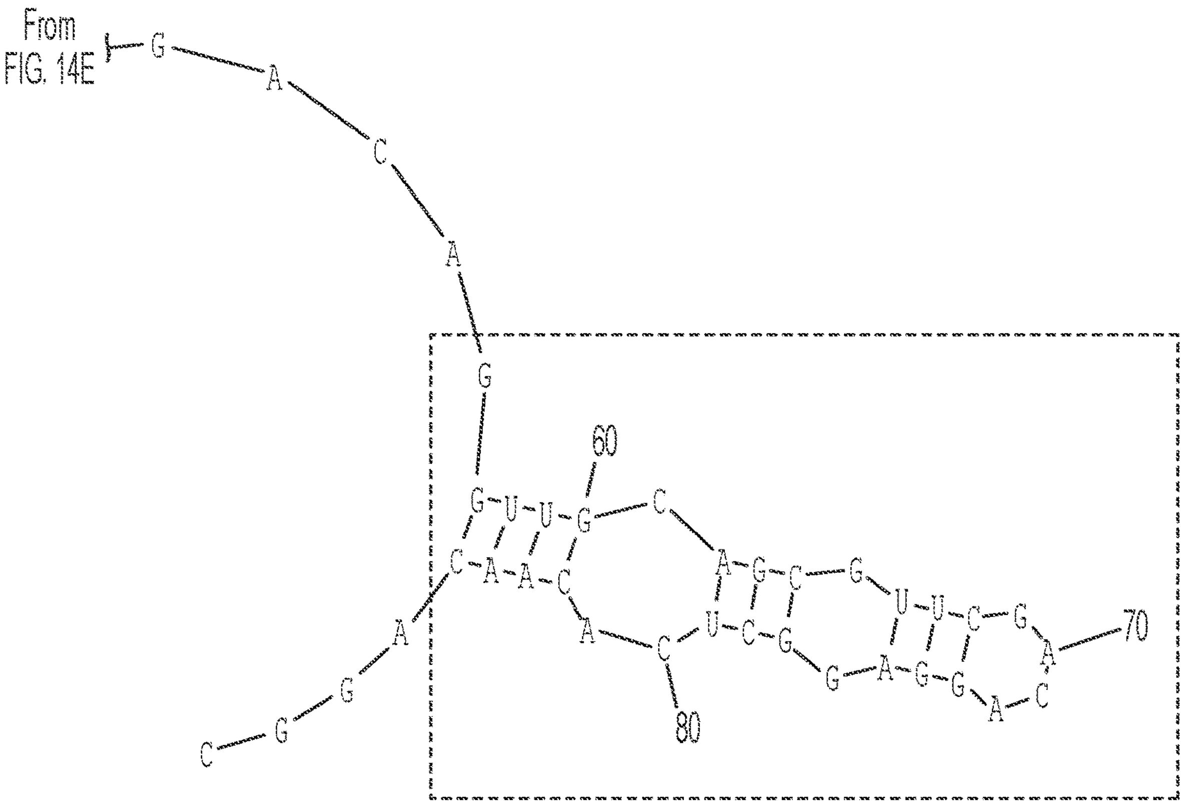
Figure 15A:
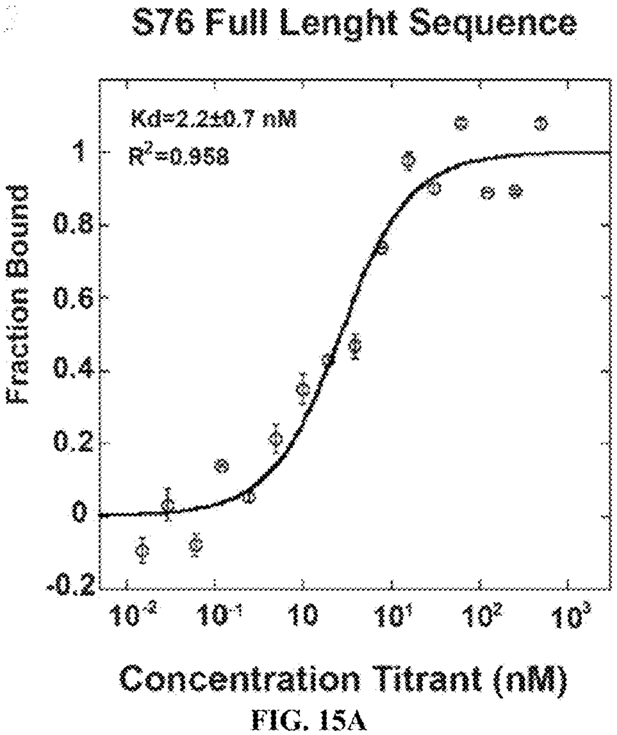
FIGS. 15A-15D. Comparison of Binding Affinity and Secondary Structure of S76 and S76.T.
Figure 15B:
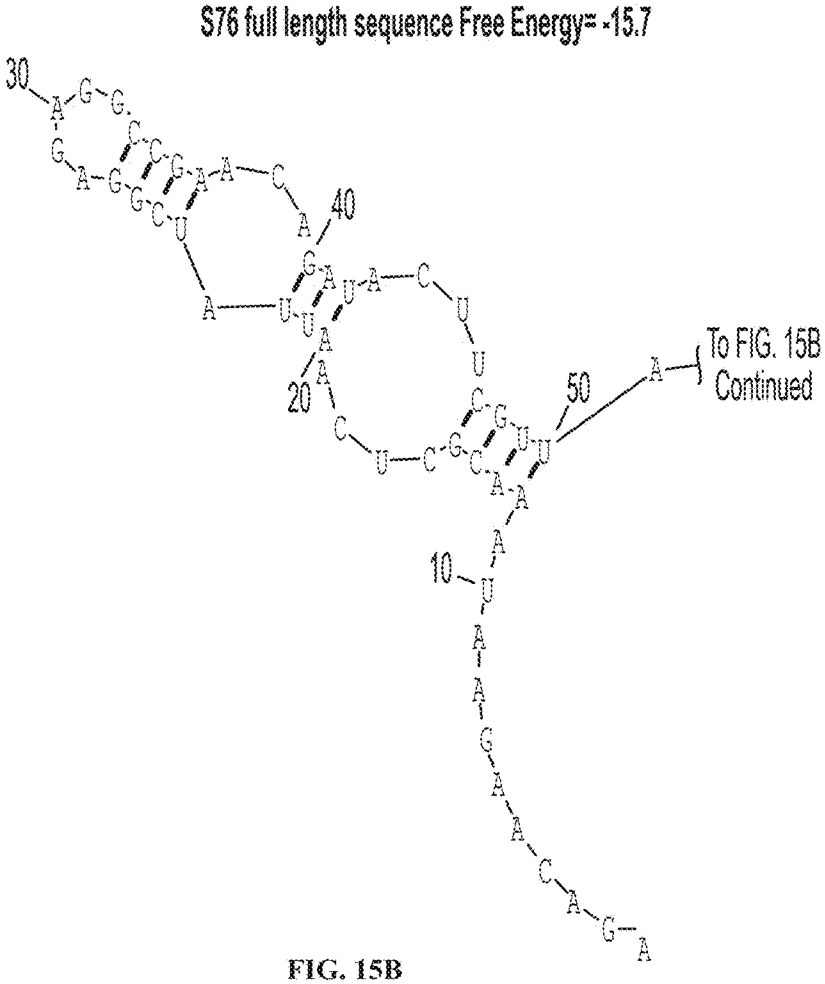
Figure 15B:
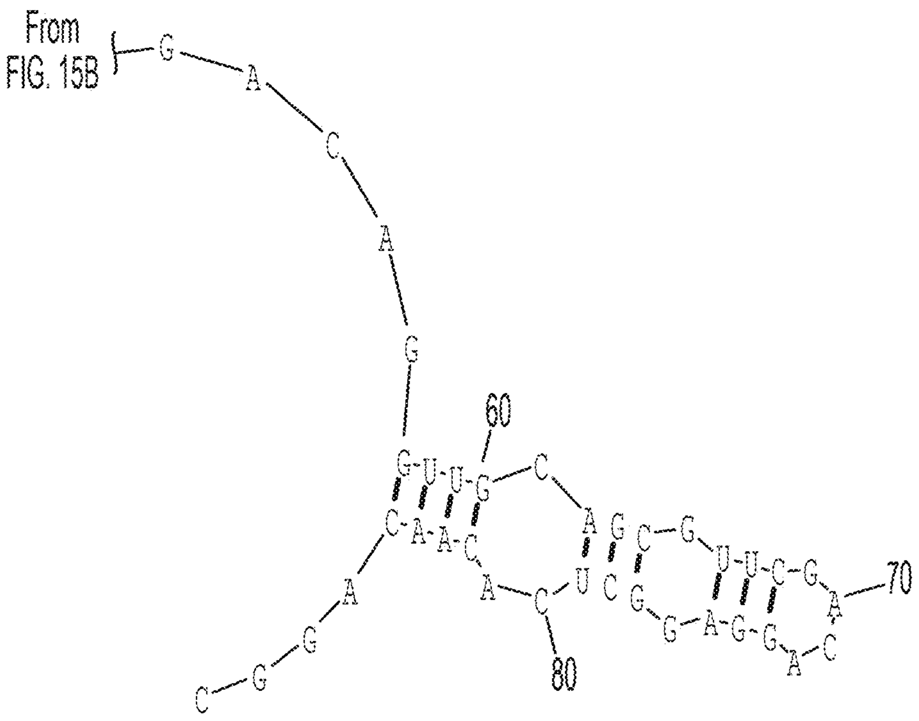
Figure 15C:
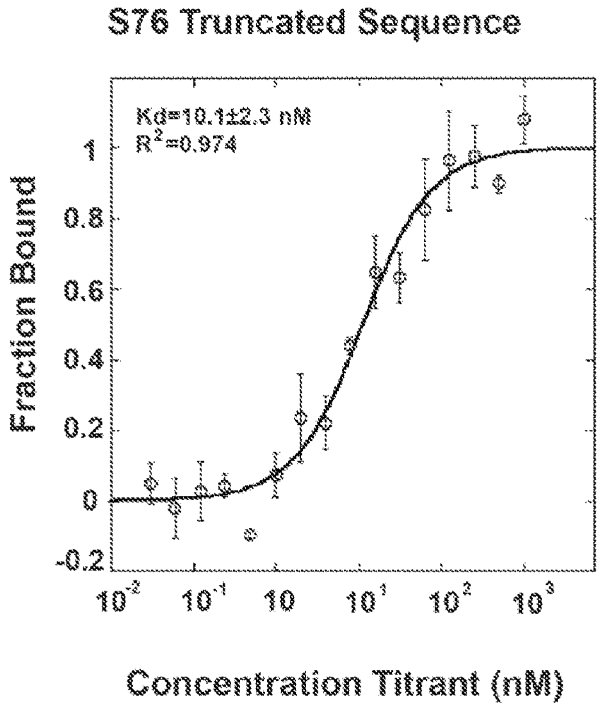
Figure 15D:
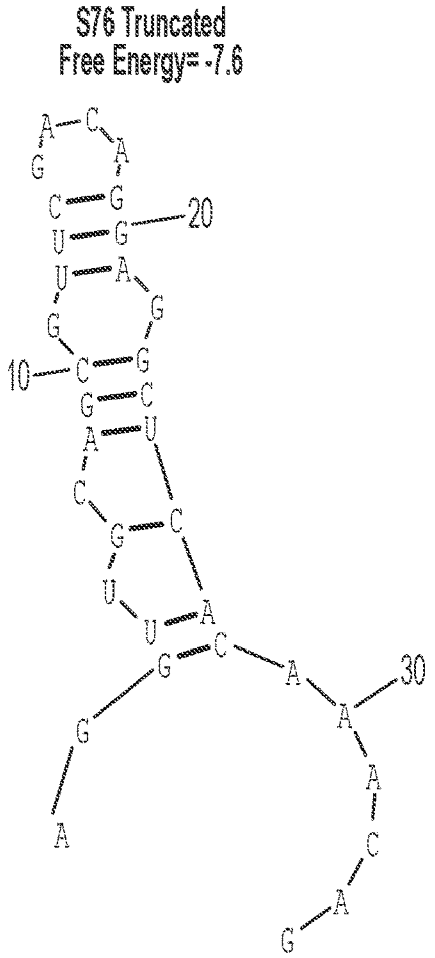

To identify a sequence with higher affinity binding for CD5L, another two cycles of protein-SELEX were performed using S5 aptamer as starting sequence (FIG. 11). Through the second cycle of selection, S11, S23, S29 and S76 were identified from the phylogenetic tree (FIG. 13A). The S11 (AGACAAGAAUAAACGCUCAAUUAUCG-GAGAGGCCGAACAGAUACUUCGUUAG ACACC-UUGCAGCGUUCGACAGGAGGC; SEQ ID NO: 2), S23 (AGACAAGAAUAAACGCU-CAAAAAGAGAGAAGGAUAAGAACCAU-CAAAAAGAG AGAGCAGAGCCAGAUUCGACAG-GAGGCUCACAACAGGC; SEQ ID NO: 3), S29 (AGACAAGAAUAAACGCU-CAAAAAGAGAGAAGGAUAAGAACCAU-CAAAAAGAG AGAGCAGAGCCAGAUUCGACAG-GAGGCUCACAACAGGC; SEQ ID NO: 4), and S76 (AGACAAGAAUAAACGCUCAAUUAUCG-GAGAGGCCGAACAGAUACUUCGUUAG ACAG-GUUGCAGCGUUCGACAGGAGGCUCACAACAGGC; SEQ ID NO: 5) sequences show points of insertion or deletion compared with the starting sequence S5 (FIG. 13B). Among all the sequences, S76 is the aptamer with the best $K_D$ value (2.2±0.7 nM) (Table 3). Next, to determine the functional part of the aptamer involved in recognition of CD5L target, the secondary structures were analyzed and a common hairpin like structure highlighted by red rectangle was identified (FIG. 14). After the truncation of the S76 sequence, named S76.T (SEQ ID NO: 6), the binding affinity was analyzed to evaluate if the truncated version could bind CD5L with the same or better affinity (FIG. 15). These data show that S76.T had a $K_D$ of 10.1±2.3 nM, which is almost comparable with the $K_D$ value of the full-length sequence S76.

TABLE 3

KD Binding Values for S11, S23 and S76 Obtained by MTS.

| Sequence Name | Kd vs. CD5L | Kd vs. VEGF |
|---|---|---|
| S11 | 59.2 +/− 22.1 nM | Weak binding indicated, not fittable |
| S23 | 92.1 +/− 40.1 nM | Weak binding indicated, not fittable |
| S76 | 2.2 +/− 0.7 nM | Weak binding indicated, not fittable |

Figure 5A:
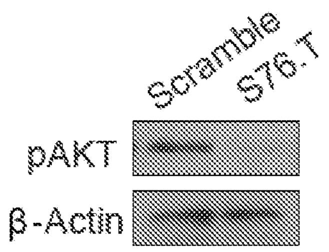
FIGS. 5A-5J. S76.T, CD5L Aptamer, Blocks the Resistance to anti-VEGF Therapy.
Figure 5B:
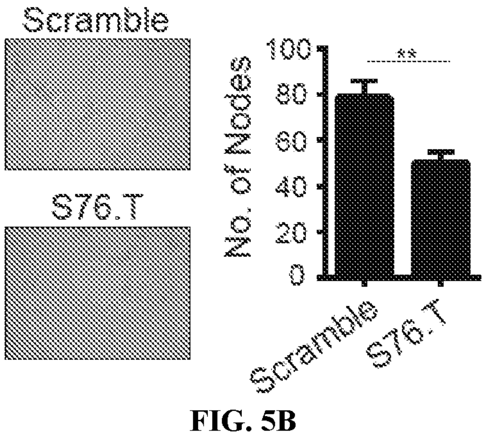
Figure 5C:
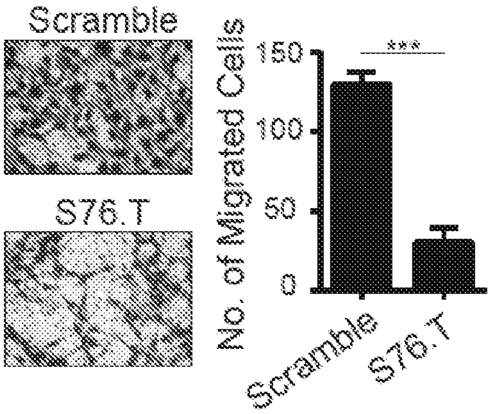
Figure 5D:
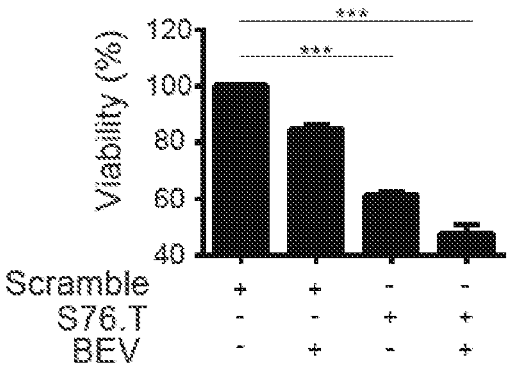

To assess the functional effects of 576.T aptamer, pAKT expression was evaluated in RF24 resistant cells following treatment with S76.T. The findings show that S76.T reduced the expression of pAKT (FIG. 5A) and significantly inhibited tube formation and cell migration (FIGS. 5B and 5C) compared to scramble aptamer in the RF24 resistant cell line. Bevacizumab-resistant RF24 cells were treated with S76.T alone or in combination with B20, an anti-VEGF drug. Combined treatment significantly reduced viability of RF24 endothelial cells compared to either treatment alone (FIG. 5D).

Figure 5E:
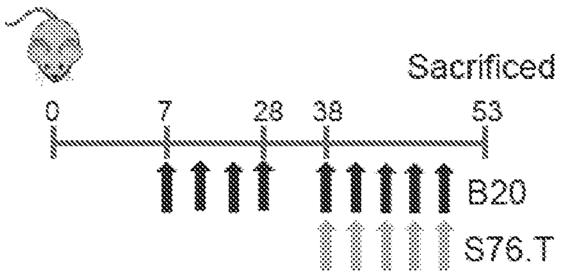
Figure 5F:
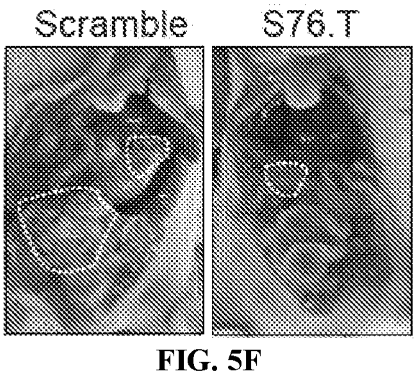
Figure 5G:
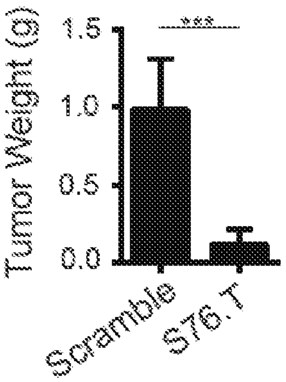
Figure 5H:
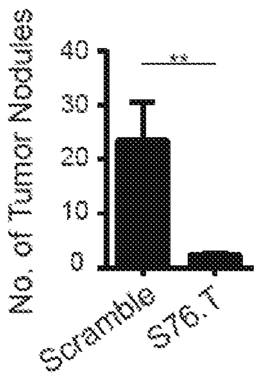
Figure 5I:
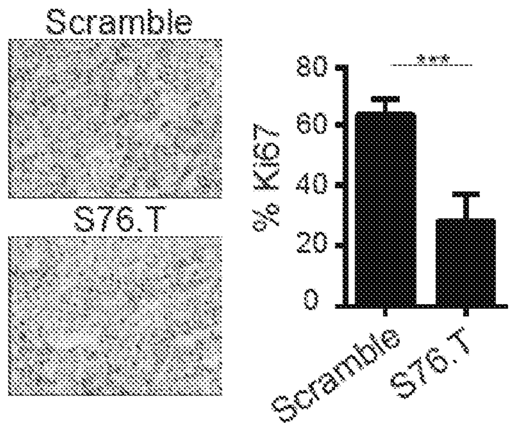
Figure 5J:
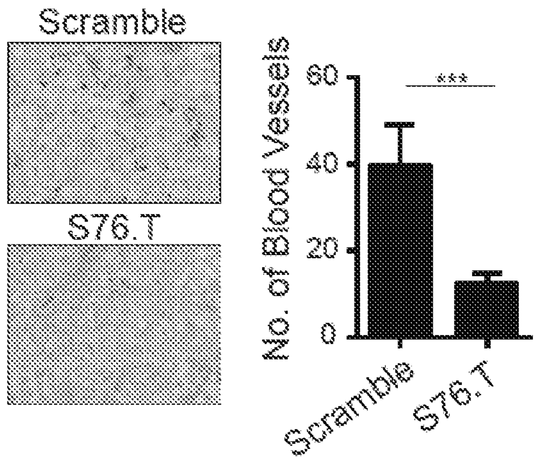

To determine the effects of S76.T in adaptive resistant tumor growth in vivo, SKOV3ip1 ovarian cancer cells were orthotopically injected into the peritoneal cavity of nude mice. To generate an adaptive resistant tumor model, tumor-bearing mice were first treated with B20 until tumor growth was noted (~4 weeks). Next, B20 treatment was combined with S76.T injected intravenously (FIG. 5E). These data demonstrate that combined treatment with S76.T reduced tumor growth compared with scrambled aptamer (FIGS. 5F and 5H). Moreover, S76.T significantly reduced cell proliferation and microvessel density (FIGS. 5I and 5J) in tumor tissues.

Figure 6A:
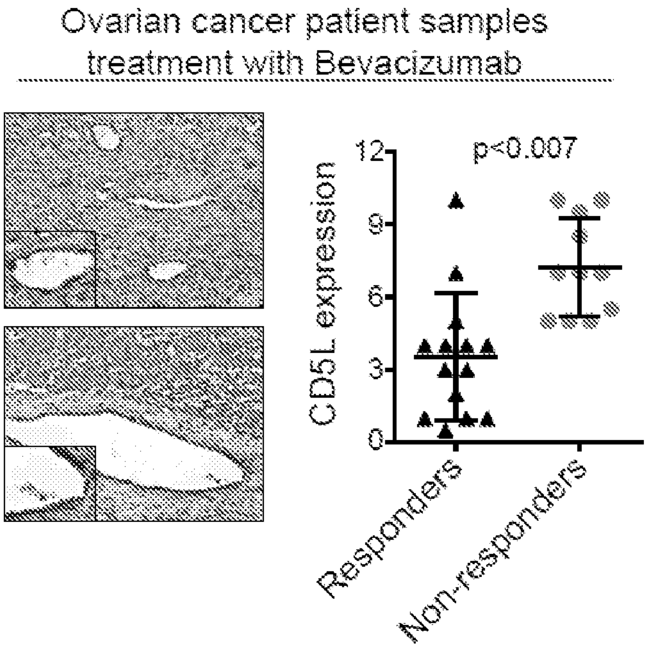
FIGS. 6A-6D. CD5L Overexpression is Associated with Bevacizumab Resistance and Worse Overall Survival in Ovarian Cancer Patients.
Figure 6B:
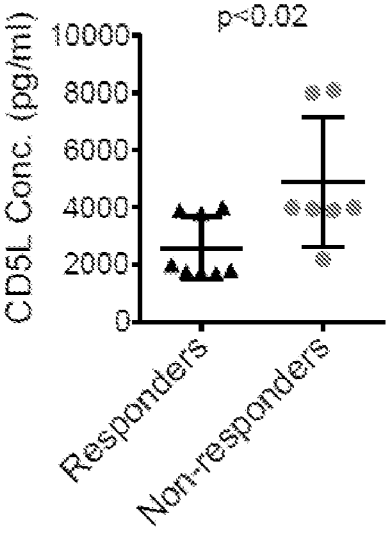
Figure 6C:
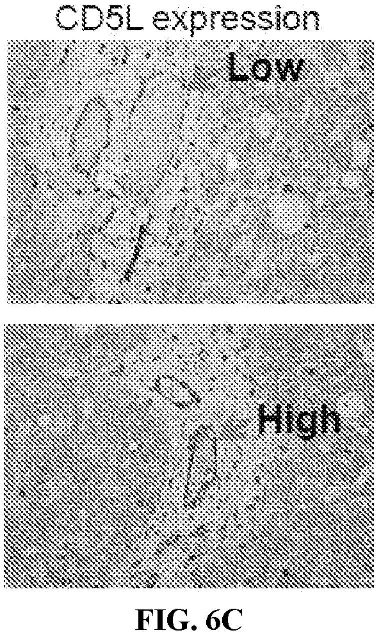
Figure 6D:
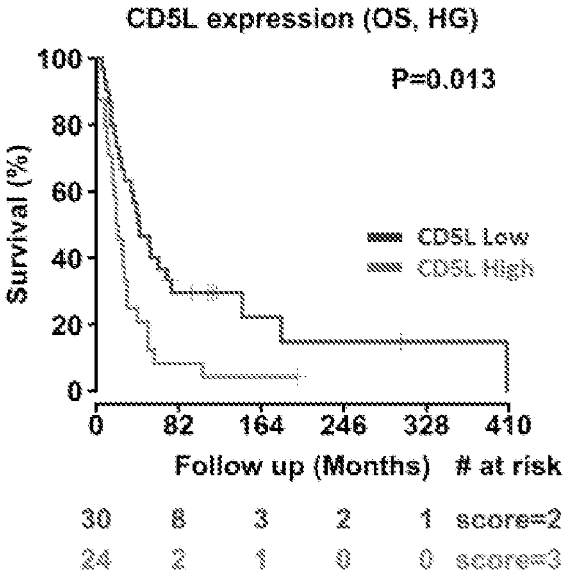

Example 7—CD5L Overexpression is Associated with Bevacizumab Resistance and Worse Overall Survival in Ovarian Cancer Patients To determine potential clinical relevance of CD5L overexpression, a select cohort of ovarian cancer patients identified as bevacizumab-responders versus non-responders was interrogated. Patients with disease resistant to bevacizumab had significantly higher CD5L expression in their tumor endothelial cells compared to those with bevacizumab-sensitive disease (FIG. 6A). Furthermore, those patients who were bevacizumab resistant also had a significantly higher serum CD5L levels compared to patients sensitive to bevacizumab treatment (FIG. 6B). In addition, IHC staining for CD5L was performed on a tissue microarray (TMA) comprised of tumor samples from an ovarian cancer cohort. CD5L expression in tumor endothelial cells ranged from absent to low (FIG. 6C, upper) to high (FIG. 6C, lower) in this cohort. Interestingly, in ovarian cancer patients with high-grade serous histology, those with high tumor endothelial CD5L expression had significantly worse overall survival than those with low expression (FIG. 6D).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

BERGERS & HANAHAN, 2008. Modes of resistance to anti-angiogenic therapy. Nat Rev Cancer, 8, 592-603.

BU et al., 2019. Human endotrophin as a driver of malignant tumor growth. JCI Insight, 5.

CASANOVAS et al., 2005. Drug resistance by evasion of antiangiogenic targeting of VEGF signaling in late-stage pancreatic islet tumors. Cancer Cell, 8, 299-309.

DONNINGER et al., 2004. Whole genome expression profiling of advance stage papillary serous ovarian cancer reveals activated pathways. Oncogene, 23, 8065-77.

FITZWATER & POLISKY, 1996. A SELEX primer. Methods Enzymol, 267, 275-301.

FOLKMAN, 1971. Tumor angiogenesis: therapeutic implications. N Engl J Med, 285, 1182-6.

GUIGNABERT et al., 2009. Tie2-mediated loss of peroxisome proliferator-activated receptor-gamma in mice causes PDGF receptor-beta-dependent pulmonary arterial muscularization. Am J Physiol Lung Cell Mol Physiol, 297, L1082-90.

HAEMMERLE et al., 2017. Platelets reduce anoikis and promote metastasis by activating YAP1 signaling. Nat Commun, 8, 310.

JOHN et al., 2018. A Novel Anti-LILRB4 CAR-T Cell for the Treatment of Monocytic AML. Mol Ther, 26, 2487-2495.

KUROKAWA et al., 2010. Macrophage-derived AIM is endocytosed into adipocytes and decreases lipid droplets via inhibition of fatty acid synthase activity. Cell Metab, 11, 479-92.

KUWATA et al., 2003. AIM inhibits apoptosis of T cells and NKT cells in *Corynebacterium*-induced granuloma formation in mice. Am J Pathol, 162, 837-47.

LAMBERTI et al., 2016. In vitro selection of RNA aptamers against CA125 tumor marker in ovarian cancer and its study by optical biosensing. Methods, 97, 58-68.

LANDEN et al., 2005. Therapeutic EphA2 gene targeting in vivo using neutral liposomal small interfering RNA delivery. Cancer Res, 65, 6910-8.

LU et al., 2010. Regulation of tumor angiogenesis by EZH2. Cancer Cell, 18, 185-97.

MAEHARA et al., 2014. Circulating AIM prevents hepatocellular carcinoma through complement activation. Cell Rep, 9, 61-74.

MIYAZAKI et al., 1999. Increased susceptibility of thymocytes to apoptosis in mice lacking AIM, a novel murine macrophage-derived soluble factor belonging to the scavenger receptor cysteine-rich domain superfamily. J Exp Med, 189, 413-22.

NARAYANA et al., 2009. Antiangiogenic therapy using bevacizumab in recurrent high-grade glioma: impact on local control and patient survival. Journal of Neurosurgery, 110, 173-180.

NOH et al., 2017. Differential Effects of EGFL6 on Tumor versus Wound Angiogenesis. Cell Rep, 21, 2785-2795.

NORDEN et al., 2008. Bevacizumab for recurrent malignant gliomas—Efficacy, toxicity, and patterns of recurrence. Neurology, 70, 779-787.

PRADEEP et al., 2015. Erythropoietin Stimulates Tumor Growth via EphB4. Cancer Cell, 28, 610-622.

QU et al., 2009. Myeloid-specific expression of Api6/AIM/Sp alpha induces systemic inflammation and adenocarcinoma in the lung. J Immunol, 182, 1648-59.

SANJURJO et al., 2015. AIM/CD5L: a key protein in the control of immune homeostasis and inflammatory disease. J Leukoc Biol, 98, 173-84.

SILVERSTEIN & FEBBRAIO, 2009. CD36, a scavenger receptor involved in immunity, metabolism, angiogenesis, and behavior. Sci Signal, 2, re3.

STOLTENBURG et al., 2015. In vitro Selection and Interaction Studies of a DNA Aptamer Targeting Protein A. PLoS One, 10, e0134403.

THAKER et al., 2006. Chronic stress promotes tumor growth and angiogenesis in a mouse model of ovarian carcinoma. Nat Med, 12, 939-44.

WEIS & CHERESH, A. 2011. Tumor angiogenesis: molecular pathways and therapeutic targets. Nat Med, 17, 1359-70.

What is claimed is:

1. An RNA aptamer that specifically binds to CD5 antigen-like precursor (CD5L), wherein the aptamer comprises SEQ ID NO:5 or SEQ ID NO:6 and has a KD value of about 20 nM or less.

2. The RNA aptamer of claim 1, further comprising at least one modified nucleotide.

3. The RNA aptamer of claim 1, where the aptamer comprises at least one 2'-modified nucleotide.

4. The RNA aptamer of claim 3, wherein at least one nucleotide is chemically modified with 2'-fluoropyrimidine.

5. The RNA aptamer of claim 3, wherein all of the pyrimidines are chemically modified with 2'-fluoro pyrimidine.

6. The RNA aptamer of claim 1, where the aptamer is covalently linked to a carrier selected from the group consisting of a soluble polymer, a biodegradable polymer, polyethylene glycol, and cholesterol.

7. The RNA aptamer of claim 1, wherein the aptamer is 40-100 nucleotides in length.

8. The RNA aptamer of claim 1, wherein the aptamer comprises SEQ ID NO:5.

9. The RNA aptamer of claim 1, wherein the aptamer comprises SEQ ID NO: 6.

10. The RNA aptamer of claim 1, wherein the aptamer is single-stranded.

11. The RNA aptamer of claim 1, wherein the aptamer folds into at least one hairpin-like structure.

12. The RNA aptamer of claim 1, wherein the aptamer further comprises a detectable label.

13. A composition comprising a therapeutically effective amount of an RNA aptamer of claim 1, and a pharmaceutically acceptable diluent or vehicle.

14. A method of treating a cancer in a patient comprising administering an effective amount of an RNA aptamer of claim 1 to the patient.

15. The method of claim 14, wherein the cancer is ovarian cancer.

16. The method of claim 14, wherein the patient's serum has been determined to have an elevated level of CD5L.

* * * * *

SEQUENCE LISTING

```
<160> NUMBER OF SEQ ID NOS: 17

<210> SEQ ID NO 1
<211> LENGTH: 89
<212> TYPE: RNA
<213> ORGANISM: Artificial Sequence
<220> FEATURE:
<223> OTHER INFORMATION: Artificial polynucleotide

<400> SEQUENCE: 1

agacaagaau aaacgcucaa gcgaaggugu gaccacaaac cacauaaagg caaggucgcg      60
```

-continued ccgcguucga caggaggcuc acaacaggc 89

<210> SEQ ID NO 2
<211> LENGTH: 78
<212> TYPE: RNA
<213> ORGANISM: Artificial Sequence
<220> FEATURE:
<223> OTHER INFORMATION: Artificial polynucleotide

<400> SEQUENCE: 2
agacaagaau aaacgcucaa uuaucggaga ggccgaacag auacuucguu agacaccuug 60
cagcguucga caggaggc 78

<210> SEQ ID NO 3
<211> LENGTH: 90
<212> TYPE: RNA
<213> ORGANISM: Artificial Sequence
<220> FEATURE:
<223> OTHER INFORMATION: Artificial polynucleotide

<400> SEQUENCE: 3
agacaagaau aaacgcucaa aaagagagaa ggauaagaac caucaaaaag agagagcaga 60
gccagauucg acaggaggcu cacaacaggc 90

<210> SEQ ID NO 4
<211> LENGTH: 90
<212> TYPE: RNA
<213> ORGANISM: Artificial Sequence
<220> FEATURE:
<223> OTHER INFORMATION: Artificial polynucleotide

<400> SEQUENCE: 4
agacaagaau aaacgcucaa aaagagagaa ggauaagaac caucaaaaag agagagcaga 60
gccagauucg acaggaggcu cacaacaggc 90

<210> SEQ ID NO 5
<211> LENGTH: 89
<212> TYPE: RNA
<213> ORGANISM: Artificial Sequence
<220> FEATURE:
<223> OTHER INFORMATION: Artificial polynucleotide

<400> SEQUENCE: 5
agacaagaau aaacgcucaa uuaucggaga ggccgaacag auacuucguu agacagguug 60
cagcguucga caggaggcuc acaacaggc 89

<210> SEQ ID NO 6
<211> LENGTH: 33
<212> TYPE: RNA
<213> ORGANISM: Artificial Sequence
<220> FEATURE:
<223> OTHER INFORMATION: Artificial polynucleotide

<400> SEQUENCE: 6
agguugcagc guucgacagg aggcucacaa cag 33

<210> SEQ ID NO 7
<211> LENGTH: 39
<212> TYPE: RNA
<213> ORGANISM: Artificial Sequence
<220> FEATURE:
<223> OTHER INFORMATION: Artificial polynucleotide -continued

<400> SEQUENCE: 7
uucguaccgg guagguuggc uugcacauag aacguguca 39

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ctgcttgttc tcctgagccc 20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
tcaaagggtc agggttgagc 20

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
gccctttggt gactttatgg a 21

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gcagcaggtt gtcttggatg 20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
gagaactgtt atggggctat 20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ttcaactgga gaggcaaagg 20

<210> SEQ ID NO 14
<211> LENGTH: 25

-continued

```
<212> TYPE: DNA
<213> ORGANISM: Artificial Sequence
<220> FEATURE:
<223> OTHER INFORMATION: Synthetic primer

<400> SEQUENCE: 14

cgcataacca gtgaaacagc attgc                                          25

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15

ccctgtgctc agacagaaat gaga                                           24

<210> SEQ ID NO 16
<211> LENGTH: 754
<212> TYPE: DNA
<213> ORGANISM: Homo sapiens

<400> SEQUENCE: 16

ataacaaatc tgtatattgg accctctgct tagcagtgag aaagcaggtt tgaagacaat     60

aaagccaggc ctgtatgtgg agattggcac catgaccctg gattatgttt tatgggatat    120

gcctccaagg gcaactctgc atttatccca tggcctctgg cttccaaatt ttctaggcac    180

ttccctctgg ggtaaaggaa tcaaaattgg cttatttccc ttgcaaacca tccttggcga    240

ctaagtactg ccttgtcttc tactgagaga tggccatatt tttggcacct gcctttcctt    300

gtgggaggtg tttcctctgt ttacatagca aaggggctgt aggagagaca gacggagctg    360

gacttacagc agaaccaagt catgatagcc tgtttctatt ttgttttcag catttttccg    420

ccagttctgg ccacctcctt tcctctggaa catgctgatt tcagcaagtc cagctctgtc    480

agctctgccc cccgagtcta ttggtttctg atcatctgat aatgctttgt ctgcactcag    540

gacctgtctt tgtccctcct cttaacatac ttgcagctaa aactaaatat tgctgcttgg    600

ggacctcctt ctagccttaa atttcagctc atcaccttca cctgccttgg tcatggctct    660

gctattctcc ttgatccttg gtgagtatct ctgcacctgt tggtttaggc ttcagagttt    720

tctggcactt tgattaggag aactttctcc ccgc                                754

<210> SEQ ID NO 17
<211> LENGTH: 15
<212> TYPE: DNA
<213> ORGANISM: Homo sapiens

<400> SEQUENCE: 17

gtcagctctg ccccc                                                     15
```